US010241108B2

(12) United States Patent
Shen et al.

(10) Patent No.: US 10,241,108 B2
(45) Date of Patent: Mar. 26, 2019

(54) ABNORMAL SYNGAMY PHENOTYPES OBSERVED WITH TIME LAPSE IMAGING FOR EARLY IDENTIFICATION OF EMBRYOS WITH LOWER DEVELOPMENT POTENTIAL

(71) Applicant: PROGYNY, INC., Menlo Park, CA (US)

(72) Inventors: Shehua Shen, Menlo Park, CA (US); Alice A. Chen Kim, Menlo Park, CA (US); Kelly Athayde Wirka, Menlo Park, CA (US); Vaishali Suraj, Menlo Park, CA (US); Lei Tan, Menlo Park, CA (US)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 14/171,610

(22) Filed: Feb. 3, 2014

(65) Prior Publication Data

US 2014/0220619 A1    Aug. 7, 2014

Related U.S. Application Data

(60) Provisional application No. 61/759,598, filed on Feb. 1, 2013, provisional application No. 61/783,958, filed on Mar. 14, 2013.

(51) Int. Cl.
G01N 33/50    (2006.01)
G01N 33/48    (2006.01)

(52) U.S. Cl.
CPC ... *G01N 33/5091* (2013.01); *G01N 2800/367* (2013.01)

(58) Field of Classification Search
CPC ........... G01N 33/5091; G01N 33/5005; G01N 2800/367
See application file for complete search history.

(56) References Cited

U.S. PATENT DOCUMENTS

| 5,541,081 A | 7/1996 | Hardy et al. |
| 5,837,543 A | 11/1998 | Conway-Myers et al. |
| 5,843,780 A | 12/1998 | Thomson et al. |
| 5,882,928 A | 3/1999 | Moses |
| 5,961,444 A | 10/1999 | Thompson |
| 6,130,086 A | 10/2000 | Nakazawa et al. |
| 6,166,761 A | 12/2000 | Arav |
| 6,200,806 B1 | 3/2001 | Thomson et al. |
| 6,281,013 B1 | 8/2001 | Grondahl |
| 6,610,543 B2 | 8/2003 | Choay et al. |
| 6,777,233 B2 | 8/2004 | Carpenter et al. |
| 7,029,913 B2 | 4/2006 | Thomson et al. |
| 7,037,892 B2 | 5/2006 | Saito et al. |
| 7,268,939 B1 | 9/2007 | McDowell |
| 7,879,539 B2 | 2/2011 | Pribenszky et al. |
| 7,963,906 B2 | 6/2011 | Wong et al. |
| 8,323,177 B2 | 12/2012 | Wong et al. |
| 8,337,387 B2 | 12/2012 | Wong et al. |
| 2003/0103662 A1 | 6/2003 | Finkbeiner |
| 2003/0138942 A1 | 7/2003 | Cecchi et al. |
| 2006/0099570 A1 | 5/2006 | Damgaard et al. |
| 2007/0087321 A1 | 4/2007 | Pribenszky et al. |
| 2008/0247628 A1 | 10/2008 | Ramsing et al. |
| 2009/0047263 A1 | 2/2009 | Yamanaka et al. |
| 2009/0068742 A1 | 3/2009 | Yamanaka et al. |
| 2009/0163764 A1 | 6/2009 | Sher et al. |
| 2010/0041090 A1 | 2/2010 | Ramsing et al. |
| 2011/0092762 A1* | 4/2011 | Wong .................. C12N 5/0604 600/34 |
| 2011/0105834 A1 | 5/2011 | Wong et al. |
| 2011/0111447 A1 | 5/2011 | Ramsing et al. |
| 2011/0165609 A1 | 7/2011 | Ramsing et al. |
| 2011/0183367 A1 | 7/2011 | Morck et al. |
| 2011/0189648 A1 | 8/2011 | Pribenszky et al. |
| 2012/0040849 A1 | 2/2012 | Simon Valles et al. |
| 2012/0094326 A1 | 4/2012 | Wong et al. |
| 2012/0095287 A1 | 4/2012 | Wong et al. |
| 2012/0123193 A1 | 5/2012 | Posillico et al. |
| 2012/0140056 A1 | 6/2012 | Pribenszky et al. |
| 2012/0196316 A1 | 8/2012 | Sebesta et al. |
| 2012/0309043 A1 | 12/2012 | Ramsing et al. |
| 2013/0023041 A1 | 1/2013 | Greenberger et al. |
| 2013/0102837 A1 | 4/2013 | Ramsing et al. |
| 2013/0162795 A1 | 6/2013 | Wong et al. |
| 2013/0165745 A1 | 6/2013 | Wong et al. |
| 2013/0337487 A1 | 12/2013 | Loewke et al. |
| 2014/0017717 A1 | 1/2014 | Loewke et al. |

FOREIGN PATENT DOCUMENTS

| CN | 101331500 A | 12/2008 |
| CN | 101495619 A | 7/2009 |
| EP | 0882225 A1 | 12/1998 |
| EP | 0941305 A1 | 9/1999 |
| EP | 1455643 A1 | 9/2004 |
| EP | 1542154 A2 | 6/2005 |
| EP | 1579209 A2 | 9/2005 |
| EP | 1667517 A1 | 6/2006 |
| EP | 1949297 A1 | 7/2008 |
| EP | 2035548 A2 | 3/2009 |
| EP | 2173853 A2 | 4/2010 |
| EP | 2282210 A1 | 2/2011 |
| EP | 2315823 A2 | 5/2011 |
| EP | 2333107 A1 | 6/2011 |
| EP | 2348318 A1 | 7/2011 |
| EP | 2452222 A2 | 5/2012 |
| EP | 2453738 A1 | 5/2012 |
| JP | 2009-512037 A | 3/2009 |
| JP | 2009-539387 A | 11/2009 |
| WO | WO 97/19345 A1 | 5/1997 |
| WO | WO 98/21309 A1 | 5/1998 |
| WO | WO 03/055385 A1 | 7/2003 |
| WO | WO 03/077552 A1 | 9/2003 |

(Continued)

OTHER PUBLICATIONS

Kahraman et al. "Pronuclear morphology scoring and chromosomal status of embryos in severe male infertility." Hum Reprod. Dec. 2002;17(12):3193-200.*

(Continued)

*Primary Examiner* — Titilayo Moloye
(74) *Attorney, Agent, or Firm* — Medlen & Carroll, LLP

(57)    ABSTRACT

Methods, compositions and kits for determining the developmental potential of one or more embryos are provided. These methods, compositions and kits find use in identifying embryos in vitro that are most useful in treating infertility in humans.

17 Claims, 4 Drawing Sheets

(56) References Cited

FOREIGN PATENT DOCUMENTS

| | | |
|---|---|---|
| WO | WO 2004/005665 A2 | 1/2004 |
| WO | WO 2004/056265 A2 | 7/2004 |
| WO | WO 2005/022996 A1 | 3/2005 |
| WO | WO 2007/042044 A1 | 4/2007 |
| WO | WO 2007/144001 A2 | 12/2007 |
| WO | WO 2008/149055 A1 | 12/2008 |
| WO | WO 2009/003487 A2 | 1/2009 |
| WO | WO 2009/125219 A2 | 10/2009 |
| WO | WO 2009/146335 A1 | 12/2009 |
| WO | WO 2010/003423 A2 | 1/2010 |
| WO | WO 2010/010201 A1 | 1/2010 |
| WO | WO 2010/010213 A1 | 1/2010 |
| WO | WO 2011/004208 A2 | 1/2011 |
| WO | WO 2011/008932 A1 | 1/2011 |
| WO | WO 2011/071551 A1 | 6/2011 |
| WO | WO 2011/089240 A1 | 7/2011 |
| WO | 2012/047678 A2 | 4/2012 |
| WO | WO 2012/042228 A2 | 4/2012 |
| WO | 2012/116185 A1 | 8/2012 |
| WO | WO 2012/163363 A1 | 12/2012 |
| WO | 2013/004239 A1 | 1/2013 |
| WO | 2013/029625 A1 | 3/2013 |

OTHER PUBLICATIONS

Yu et al. "Effects of combined epidermal growth factor, brain-derived neurotrophic factor and insulin-like growth factor-1 on human oocyte maturation and early fertilized and cloned embryo development." Hum Reprod. Jul. 2012;27(7):2146-59.*
Shaw et al. "Comparison of gene expression in fresh and frozen-thawed human preimplantation embryos." Reproduction. Nov. 2012;144(5):569-82.*
Definition of automated. accessed from vocabulary.com on Aug. 21, 2015.*
Nicoli et al. "Pronuclear morphology evaluation in in vitro fertilization (IVF) / intracytoplasmic sperm injection (ICSI) cycles: a retrospective clinical review." J Ovarian Res. Jan. 3, 2013;6(1):1.*
Scott et al. "The successful use of pronuclear embryo transfers the day following oocyte retrieval." Hum Reprod. Apr. 1998;13(4):1003-13.*
Lawler et al. "Relationships between timing of syngamy, female age and implantation potential in human in vitro-fertilised oocytes." Reprod Fertil Dev. 2007;19(3):482-7.*
Iwata et al. "Dynamic analysis of the relationship between the timing of syngamy and human embryonic development using time-lapse cinematography." Fertility and Sterility, vol. 98, Issue 3, S164. Sep. 2012 (Year: 2012).*
Mio et al. "Time-lapse cinematography of dynamic changes occurring during in vitro development of human embryos." Am J Obstet Gynecol. Dec. 2008;199(6):660.e1-5. Reproductive Centre, Mio fertility clinic, Yonago, Tottori, JapanP-178 Tuesday, Oct. 23, 2012 (Year: 2008).*
Balaban et al. "The Istanbul consensus workshop on embryo assessment: proceedings of an expert meeting . . . " Hum Reprod. Jun. 2011;26(6):1270-83. (Year: 2011).*
U.S. Appl. No. 61/236,085, filed Aug. 22, 2009, Wong et al.
U.S. Appl. No. 61/332,651, filed May 7, 2010, Wong et al.
"Human embryo which gave a vital pregnancy. Embryo Cleavage Rating (ECR)". Video uploaded to youtube.com by HlinkaDaniel on Apr. 14, 2010 (http://www.youtube.com/watch?v=61nr4HWiz9M), 2 pages.
"Guide to Publication Policies of the Nature Journals—Editorial Policies—Nature Journals' Policies on Publication Ethics," 20 pages (Last updated Feb. 13, 2012).
"Guide to the Authors," Nature Biotechnology, 9 pages (Revised Feb. 29, 2012).
3rd Party Submission for European Application No. 10748194.4 (dated Oct. 18, 2011).

Abeydeera, L. R., "In Vitro Production of Embryos in Swine," Theriogenology, 57:257-273 (2002).
Aboulghar, M. M. et al., "Pregnancy rate is not improved by delaying embryo transfer from days 2 to 3," European Journal of Obstetrics & Gynecology and Reproductive Biology, 107:176-179 (2003).
Adachi et al., "Analysis of Physiological Process in Early Stage of Human Embryos after ICSI using Time-lapse Cinematography," J. Mamm. Ova. Res. 22:64-70 (2005).
Alikani, M. et al., "Cleavage anomalies in early human embryos and survival after prolonged culture in-vitro," Hum. Reprod., 15(12):2634-2643 (2000).
Alikani, M. et al., "Cytoplasmic fragmentation in activated eggs occurs in the cytokinetic phase of the cell cycle, in lieu of normal cytokinesis, and in response to cytoskeletal disorder," Mol. Hum. Reprod., 11(5):335-344 (2005).
Alikani, M. et al., "Human embryo fragmentation in vitro and its implications for pregnancy and implantation," Fertil. Steril., 71(5):836-842 (1999).
Alpha Scientists, "The Istanbul consensus workshop on embryo assessment: proceedings of an expert meeting," Human Reproduction, 26(6):1270-1283 (2011).
Altman Amd Royston, "What do we mean by validating a prognostic model?" Stat. Med. 19:453-473 (2000).
Alvarez, C. et al., "Zygote score and status 1 or 2 days after cleavage and assisted reproduction outcome," Int. J. Gynecol. Obstet., 101:16-20 (2008).
Ambartsumyan, G. et al., "Aneuploidy and early human embryo development," Human Molecular Genetics, 17(1):R10-R15 (2008).
American Journal of Obstetrics & Gynecology's website regarding Mio (2008) (2012), 2 pages.
Andersen, A. N. et al., "Assisted reproductive technology in Europe, 2004: results generated from European registers by ESHRE," Hum. Reprod., 23(4):756-771 (2008).
Anoraganingrum, D., "Cell segmentation with median filter and mathematical morphology operation," Proceedings of International Conference on Image Analysis and Processing, pp. 1043-1046 (1999).
Antczak, M. et al., "Oocyte influences on early development: the regulatory proteins leptin and STAT3 are polarized in mouse and human oocytes and differentially distributed within the cells of the preimplantation stage embryo," Mol. Hum. Reprod., 3(12):1067-1086 (1997).
Antczak, M. et al., "Temporal and spatial aspects of fragmentation in early human embryos: possible effects on developmental competence and association with the differential elimination of regulatory proteins from polarized domains," Human Reprod., 14:429-447 (1999).
Aprysko, V. P. et al., "Noninvasive selection of euploid embryos with high implantation potential based on synchronism of blastomere cleavage," Abstracts of the 26th Annual Meeting of ESHRE, P-206:i196-i197 (2010).
Arav, A., "Prediction of embryonic developmental competence by time-lapse observation and shortest-half analysis," Reproductive Biomedicine Online, 17(5):669-675, Article 3412 (Sep. 30, 2008).
ASRM Website, http://www.asrm.org/; Copyright 1996-2012 ASRM, American Society for Reproductive Medicine.
Atasoy, S. et al., "A Global Approach for Automatic Fibroscopic Video Mosaicing in Minimally Invasive Diagnosis," Proceedings of MICCAI, pp. 850-857 (2008) (contains duplicate pages for figure clarity).
Baart, E. B. et al., "Fluorescence in situ hybridization analysis of two blastomeres from day 3 frozen-thawed embryos followed by analysis of the remaining embryo on day 5," Hum. Reprod., 19(3):685-693 (2004).
Baart, E. B. et al., "Preimplantation genetic screening reveals a high incidence of aneuploidy and mosaicism in embryos from young women undergoing IVF," Hum Reprod., 21(1):223-233 (2006).
Bahceci, M. et al., "Efficiency of changing the embryo transfer time from day 3 to day 2 among women with poor ovarian response: A prospective randomized trial," Fertility and Sterility, 86(1):81-85 (2006).

(56) References Cited

OTHER PUBLICATIONS

Balaban, B. et al., "Effect of oocyte morphology on embryo development and implantation," Reproductive BioMedicine Online, 12(5):608-615 (2006).
Baltaci, V. et al., "Relationship between embryo quality and aneuploidies," Reprod. BioMed. Online, 12(1):77-82 (2006).
Barbash-Hazan, S. et al., "Preimplantation aneuploid embryos undergo self-correction in correlation with their developmental potential," Fertil. Steril., 92(3):890-896 (2009).
Basile, N. et al., "Time lapse technology: evaluation of embryo quality and new markers for embryo selection," Expert Rev. Obstet. Gynecol., 7(2):175-190 (2012).
Basille et al., "Preimplantation genetic diagnosis: State of the art," Eur. J. Obstet. Gynecol. Reprod. Biol. 145:9-13 (2009).
Bavister, B. D. et al., "Duration and temperature of culture medium equilibration affect frequency of blastocyst development," Reprod. BioMed. Online, 10(1):124-129 (2004).
Bavister, B., "The role of animal studies in supporting human assisted reproductive technology," Reprod. Fertil. Dev., 16:719-728 (2004).
Baxter Bendus, A. E. et al., "Interobserver and intrabserver variation in day 3 embryo grading," Fertility and Sterility, 86(6):1608-1615 (2006).
Becker, V. et al., "High-resolution miniprobe-based confocal microscopy in combination with video mosaicing," Gastrointestinal Endoscopy, 66(5):1001-1007 (2007).
Beddington, R. S. P. et al., "An assessment of the developmental potential of embryonic stem cells in the midgestation mouse embryo," Development, 105:733-737 (1989).
Behr, B. et al., "Metebolomic profile of human oocyte is predictive to embryo development and viability," Abstracts of the $24^{th}$ Meeting of the ESHRE, O-205:i83 (2008).
Ben-Yosef, D. et al., "Prospective Randomized Comparison of Two Embryo Culture Systems: P1 Medium by Irvine Scientific and the Cook IVF Medium," J. Assist. Reprod. Genet., 21(8):291-295 (2004).
Bischoff, M. et al., "Formation of the embryonic-abembryonic axis of the mouse blastocyst: relationships between orientation of early cleavage divisions and pattern of symmetric/asymmetric divisions," Development, 135:953-962 (2008).
Boiso et al., (2002) "Fundamentals of Human Embryonic Growth in vitro and the selection of high-quality embryos for transfer" Reproductive BioMedicine Online, 5(3):328-350.
Booth, P. J. et al., "Prediction of Porcine Blastocyst Formation Using Morphological, Kinetic, and Amino Acid Depletion and Appearance Criteria Determined During the Early Cleavage of in Vitro-Produced Embryos," Biology of Reproduction, 77:765-779 (2007).
Bos-Mikich et al., (2001) "Early cleavage of human embryos: an effective method for predicting successful IVF/ICSI outcome," Human Reprod. 16(12):2658-2661.
Brezinova, et al. (2009) "Evaluation of day one embryo quality and IVF outcome—a comparison of two scoring systems," Reproductive Biology and Endocrinology, 7:9-14.
Brison, D. R. et al., "Predicting human embryo viability: the road to non-invasive analysis of the secretome using metabolic footprinting," Reprod. BioMed. Online, 15(3):296-302 (2007).
Bromer, J. G. et al., "Assessment of embryo viability in assisted reproductive technology: shortcomings of current approaches and the emerging role of metabolomics," Curr. Opin. Obstet. Gynecol., 20:234-241 (2008).
Chavez et al., "Dynamic blastomere behaviour reflects human embryo ploidy by the four-cell stage," Nature Commun. 3, Article No. 1251 (2012) doi:10.1038/ncomms2249.
Chenouard, N. et al., "Improving 3D tracking in microscopy by joint estimation of kinetic and image models," MICCAI Workshop on MIAAB (2008).
Clinic Summary Report, All SART Member Clinics, The Society of Assisted Reproductive Technology ("SART") 2010 statistics as published on the SART website (2012), 1 page.
Coy, P. et al., "In vitro production of pig embryos: a point of view," Reprod. Fertil. Dev., 14:275-286 (2002).
Cruz, M. et al., "Embryo quality, blastocyst and ongoing pregnancy rates in oocyte donation patients whose embryos were monitored by time-lapse imaging," J. Asssit. Reprod. Genet., 28:569-573 (2011).
Cruz, M. et al., "Timing of cell divisions in human cleavage-stage embryos correlates with blastocyst formation and quality," Reprod. BioMed. Online, Accepted Manuscript:26 pages (2012).
Cummins, et al. (1986) "A formula for scoring human embryo growth rates in in vitro fertilization: Its value in predicting pregnancy and in comparison with visual estimates of embryo quality," Journal of In Vitro Fertilization and Embryo Transfer, 3(5):284-295.
De Los Santos, J. M. et al., "Development of tripronucleated ICSI-derived embryos using real time assessment," Abstracts of the $26^{th}$ Annual Meeting of ESHRE, P-196:i192 (2010).
De Los Santos, M. J. et al., "Implantation Rates after Two, Three, or Five Days of Embryo Culture," Placenta, 24:S13-S19 (2003).
Declaration of Prof. Markus Montag Under 37 C.F.R. § 1.132 (dated Oct. 13, 2011).
Desai, N. et al., "Granulocyte-macrophage colony stimulating factor (GM-CSF) and co-culture can affect post-thaw development and apoptosis in cryopreserved embryos," J. Assist. Reprod. Genet., 24:215-222 (2007).
Dominko, T. et al., "Dynamic Imaging of the Metaphase II Spindle and Maternal Chromosomes in Bovine Oocytes: Implications for Enucleation Efficiency Verification, Avoidance of Parthenogenesis, and Successful Embryogenesis," Biology of Reproduction, 62:150-154 (2000).
Dumoulin, J. C. et al., "Effect of in vitro culture of human embryos on birthweight of newborns," Hum. Reprod., 25(3):605-612 (2010).
Dykstra, B. et al., "High-resolution video monitoring of hematopoietic stem cells cultured in single-cell arrays identifies new features of self-renewal," PNAS, 103(21):8185-8190 (2006).
Ebner, T. et al., "Embryo fragmentation in vitro and its impact on treatment and pregnancy outcome," Fertil. Steril., 76(2):281-285 (2001).
Edwards, B. et al., "Initial differentiation of blastomeres in 4-cell human embryos and its significance for early embryogenesis and implantation," Reprod. BioMed. Online, 11(2):206-218 (2005).
Edwards, R. G. et al., "Early Stages of Fertilization in vitro of Human Oocytes Matured in vitro," Nature, 221:632-635 (1969).
Email from the managing editor of Fertility and Sterility (Aug. 1, 2012), 1 page.
European Search Report, 7 pages, EP appl. No. 13152098.3 (dated Jun. 19, 2013).
Fancsovits, et al., (2006) "Examination of Early Cleavage and its Importance in IVF Treatment," Journal Reproduktionsmed Endokrinol, 3(6):367-372.
Fancsovits, P. et al., "Early pronuclear breakdown is a good indicator of embryo quality and viability," Fertil. Steril., 84(4):881-887 (2005).
Fauque, P. et al., "Pregnancy outcome and live birth after IVF and ICSI according to embryo quality," J. Assist. Reprod. Genet., 24:159-165 (2007).
Fenwick, et al., (2002) "Time from insemination to first cleavage predicts developmental competence of human preimplantation embryos in vitro," Human Reproduction, 17(2):407-412.
Fisch, et al. (2001) "The graduated embryo score (GES) predicts blastocyst formation and pregnancy rate from cleavage stage embryos" Hum. Reprod. 16(9):1970-1975.
Fotos et al., "Automated time-lapse microscopy and high-resolution tracking of cell migration," Cytotechnology 51:7-19 (2006).
Fragouli, E. et al., "Comparative genomic hybridization analysis of human oocytes and polar bodies," Hum. Reprod., 21:2319-2328 (2006).
Fragouli, E. et al., "Comprehensive chromosome screening of polar bodies and blastocysts from couples experiencing repeated implantation failure," Fertil. Steril., 94(3):875-887 (2010).
Fragouli, E. et al., "Increased susceptibility to maternal aneuploidy demonstrated by comparative genomic hybridization analysis of human MII oocytes and first polar bodies," Cytogenetic and Genome Res., 114:30-38 (2006).

(56) References Cited

OTHER PUBLICATIONS

Frumkin, T. et al., "Elucidating the origin of chromosomal aberrations in IVF embryos by preimplantation genetic analysis," Mol. Cell. Endocrinol., 282:112-119 (2008).
Gardner, D. K. et al., "Assessment of Embryo Viability: The Ability to Select a Single Embryo for Transfer—a Review," Placenta, 24:S5-S12 (2003).
Gardner, D. K. et al., "Textbook of Assisted Reproduction Techniques," Preface, Introduction, Chapter 2, Chapter 10, and Chapter 16 (2001).
Gardner, R. L., "Specification of embryonic axes begins before cleavage in normal mouse development," Development, 128:839-847 (2001).
Gardner, R. L., "The early blastocyst in bilaterally symmetrical and its axis of symmetry is aligned with the animal-vegetal axis of the zygote in the mouse," Development, 124:289-301 (1997).
Geber, S. et al., "Proliferation of blastomeres from biopsied cleavage stage human embryos in vitro: an alternative to blastocyst biopsy for preimplantation diagnosis," Hum. Reprod., 10:1492-1496 (1995).
Giorgetti, C. et al., "Early cleavage: an additional predictor of high implantation rate following elective single embryo transfer," Reprod. BioMed. Online, 14(1):85-91 (2007).
Gonzales, D. S. et al., "Prediction of the developmental potential of hamster embryos in vitro by precise timing of the third cell cycle," J. Reprod. Fertil., 105(1):1-8 (1995).
Gonzales, D. S. et al., "Trophectoderm projections: a potential means for locomotion, attachment and implantation of bovine, equine and human blastocysts," Hum. Reprod., 11(12):2739-2745(1996).
Gray, D. et al., "First Cleavage of the Mouse Embryo Responds to Change in Egg Shape at Fertilization," Current Biology, 14:397-405 (2004).
Grisart, B. et al., "Cinematographic analysis of bovine embryo development in serum-free oviduct-conditioned medium," J. Reprod. Fertil., 101(2):257-264 (1994).
Guerif, et al. (2002) "Parameters guiding selection of best embryos for transfer after cryopreservation: a reappraisal," Human Reprod. 17(5):1321-1326.
Guerif, et al. (2007) "Limited value of morphological assessment at days 1 and 2 to predict blastocyst development potential: a prospective study based on 402 embryos," Human Reprod. 22(7):1973-1981.
Guerif, F. et al., "Single Day 2 embryo versus blastocyst-stage transfer: a prospective study integrating fresh and frozen embryo transfers," Human Reproduction, 24(5):1051-1058 (2009).
Hahnel, D. et al., "An Extension of the ICP Algorithm for Modeling Nonrigid Objects with Mobile Robots," Proc. of IJCAI-03, pp. 915-920 (2003).
Handyside, A. H., "Pregnancies from biopsied human preimplantation embryos sexed by Y-specific DNA amplification," Nature, 344:768-770 (1990).
Handyside, A. H., "Time of commitment of inside cells isolated from preimplantation mouse embryos," J. Embryol. Exp. Morphol., 45:37-53 (1978).
Hardarson, T. et al., "Human embryos with unevenly sized blastomeres have lower pregnancy and implantation rates: indications for aneuploidy and multinucleation," Human Reproduction, 16(2):313-318 (2001).
Hardarson, T. et al., "Internalization of cellular fragments in a human embryo: time-lapse recordings," Reprod. BioMed. Online, 5(1):36-38 (2002).
Hardy, K. et al., "From cell death to embryo arrest: Mathematical models of human preimplantation embryo development," PNAS, 98(4):1655-1660 (2001).
Hardy, K. et al., "Human preimplantation development in vitro is not adversely affected by biopsy at the 8-cell stage," Hum. Reprod., 5(6):708-714 (1990).
Hardy, K. et al., "Maintenance of the Inner Cell Mass in Human Blastocysts from Fragmented Embryos," Biol. Reprod., 68:1165-1169 (2003).
Hardy, K. et al., "The human blastocyst: cell number, death and allocation during late preimplantation development in vitro," Development, 107:597-604 (1989).
Harrell Jr. et al., "Tutorial in Biostatistics. Multivariable Prognostic Models: Issues in Developing Models, Evaluating Assumptions and Adequacy, and Measuring and Reducing Errors," Sta. Med. 15:361-387 (1996).
Hashimoto, S. et al., "Selection of high-potential embryos by culture in poly(dimethylsiloxane) microwells and time-lapse imaging," Fert. and Steril., 97(2):332-337 (2012).
Heid, P. J. et al., "3D-DIASemb: A Computer-Assisted System for Reconstructing and Motion Analyzing in 4D Every Cell and Nucleus in a Developing Embryo," Developmental Biology, 245:329-347 (2002).
Heindryckx, B. et al., "Embryo development after successful somatic cell nuclear transfer to in vitro matured human germinal vesicle oocytes," Hum. Reprod., 22(7):1982-1990 (2007).
Hesters et al., "Impact of early cleaved zygote morphology on embryo development and in vitro fertilization-embryo transfer outcome: a prospective study," Fertil. Steril. 89(6):1677-1684 (2008).
Hiiragi, T. et al., "First cleavage plane of the mouse egg is not predetermined but defined by the topology of the two apposing pronuclei," Nature, 430:360-364 (2004).
Hinkins et al., "Expression of Polycomb-group genes in human ovarian follicles, oocytes and preimplantation embryos," Reproduction 130:883-888 (2005).
Hiraoka, L. et al., "Spindle-Pole Organization during Early Mouse Development," Devel. Biol., 133:24-36 (1989).
Hlinka, D. et al., "Permanent embryo monitoring and exact timing of early cleavages allow reliable prediction of human embryo viability," Abstracts of the 26$^{th}$ Annual Meeting of ESHRE, P-176:i184-i185 (2010).
Hlinka et al., "Time-Lapse Cleavage Rating Predicts Human Embryo Viability," Physiol. Res. 61:513-525 (2012).
Hnida, C. et al., "Computer-controlled, multilevel, morphometric analysis of blastomere size as biomarker of fragmentation and multinuclearity in human embryos," Human Reproduction, 19(2):288-293 (2004).
Hnida, C. et al., "Total Cytoplasmic Volume as Biomarker of Fragmentation in Human Embryos," Journal of Assisted Reproduction and Genetics, 21(9):335-340 (2004).
Hnida, C. et al., "Traditional detection versus computer-controlled multilevel analysis of nuclear structures from donated human embryos," Human Reproduction, 20(3):665-671 (2005).
Hogan, B. et al., "In vitro development of inner cell masses isolated immunosurgically from mouse blastocysts. J. Inner cell masses from 3.5- to 4.0-day p.c. blastocysts incubated for 24 h before immunosurgery," J. Embryol. Exp. Morphol., 45:107-121 (1978).
Holm, et al. (1998) "Developmental kinetics of the first cell cyles of bovine in vitro produced embryos in relation to their in vitro viability and sex," Theriogenology 50:1285-1299.
Holm, P. et al., "In vivo versus in vitro produced bovine ova: similarities and differences relevant for practical application," Reprod. Nutr. Dev., 38:579-594 (1998).
Holm, P. et al., "Kinetics of early in vitro development of bovine in vivo- and in vitro-derived zygotes produced and/or cultured in chemically defined or serum-containing media," Reproduction, 123:553-565 (2002).
Honda, H. et al., "Computer simulation of emerging asymmetry in the mouse blastocyst," Development, 135:1407-1414 (2008).
International Preliminary Report on Patentability for International Application No. PCT/US2010/046343, 7 pages (dated Feb. 28, 2012).
International Search Report, PCT appl. No. PCT/US2012/026328, 4 pages (dated Aug. 3, 2012).
International Search Report, PCT appl. No. PCT/US2013/043639, 3 pages (dated Nov. 22, 2013).
Jang, M-S. et al., "Shape Recognition of the Embryo Cell Using Deformable Template for Micromanipulation," R. Orchard et al. (Eds.): IEA/AIE 2004, LNAI 3029, pp. 463-472 (2004).
Johnson, D. S. et al., "Preclinical validation of a microarray method for full molecular karyotyping of blastomeres in a 24-h protocol," Hum. Reprod., 25(4):1066-1075 (2010).

(56) References Cited

OTHER PUBLICATIONS

Johnson, M. H. et al., "Cell Interactions Influence the Fate of Mouse Blastomeres Undergoing the Transition from 16- to the 32-Cell Stage," Devel. Biol., 95:211-218 (1983).
Johnson, M. H. et al., "Lineage allocation and cell polarity during mouse embryogenesis," Sem. Cell. Devel. Biol., 15:583-597 (2004).
Jones, G. M. et al., "Novel strategy with potential to identify developmentally competent IVF blastocysts," Hum. Reprod., 23(8):1748-1759 (2008).
Jun, et al (2008) "Defining human embryo phenotypes by cohort-specific prognostic factors," PlosOne 3(7):284-290.
Justice et al., "Assessing the Generalizability of Prognostic Information," Ann. Intern. Med. 130:515-524 (1999).
Katz-Jaffe, M. G. et al., "A proteomic analysis of mammalian preimplantation embryonic development," Reproduction, 130:899-905 (2005).
Katz-Jaffe, M. G. et al., "Analysis of protein expression (secretome) by human and mouse preimplantation embryos," Fertility and Sterility, 86(3):678-685 (2006).
Katz-Jaffe, M. G. et al., "Proteomic analysis of individual human embryos to identify novel biomarkers of development and viability," Fertility and Sterility, 85(1):101-107 (2006).
Katz-Jaffe, M. G. et al., "Relationship between cleavage stage morphology and comprehensive chromosome constitution," Abstracts of the 26th Annual Meeting of ESHRE, P-146:i172 (2010).
Katz-Jaffe, M. G. et al., "Symposium: Innovative techniques in human embryo viability assessment—Can proteomics help to shape the future of human assisted conception?," Reprod. BioMed. Online, 17(4):497-501 (2008).
Katz-Jaffe, M. G. et al., "The role of proteomics in defining the human embryonic secretome," Molecular Human Reproduction, 15(5):271-277 (2009).
Keltz, M. D. et al., "Predictors of embryo fragmentation and outcome after fragment removal in in vitro fertilization," Fertility and Sterility, 86(2):321-324 (2006).
Kidder, G. M. et al., "Timing of Transcription and Protein Synthesis Underlying Morphogenesis in Preimplantation Mouse Embryos," Devel. Biol., 112:265-275 (1985).
Kiessling, A. A., "Timing is everything in the human embryo," Nature Biotechnology, 28:1025-1026 (2010).
Kirkegaard, K. et al., "Human embryonic development after blastomere removal: a time-lapse analysis," Hum. Reprod., 27:97-105 (2012).
Kirkegaard, K. et al., "Time-lapse monitoring as a tool for clinical embryo assessment," Human Reproduction, 27(5):1277-1285 (2012).
Kuo, H-C. et al., "Chromosomal mosaicism in cleavage-stage human embryos and the accuracy of single-cell genetic analysis," J. Assist. Reprod. Genet., 15(5):276-280 (1998).
Kurimoto, K. et al., "An improved single-cell cDNA amplification method for efficient high-density oligonucleotide microarray analysis," Nucleic Acids Research, 34(5):e42 (2006), 17 pages.
Kurotaki, Y. et al., "Blastocyst Axis Is Specified Independently of Early Cell Lineage But Aligns with the ZP Shape," Science 316:719-723 (2007).
Langenberg, T. et al., "Imaging Brain Development and Organogenesis in Zebrafish Using Immobilized Embryonic Explants," Developmental Dynamics, 228:464-474 (2003).
Lathi, R. B. et al., "Pregnancy after trophectoderm biopsy of frozen-thawed blastocyst," Fertility and Sterility, 91(5):1938-1940 (2009).
Lavoir, M. et al., "Poor development of human nuclear transfer embryos using failed fertilized oocytes," Reprod. BioMed. Online, 11(6):740-744 (2005).
Lawson, K., "Fate mapping the mouse embryo," Int. J. Dev. Biol., 43:773-775 (1999).
Le Gac, S. et al., "Development of integrated microfluidic chips for single embryo physiology studies," Abstracts of the 26th Annual Meeting of ESHRE, P-159:i177 (2010).
Lechniak et al., "Timing of the first zygotic cleavage as a marker of developmental potential of mammalian embryos," Reprod. Biol. 8(1):23-42 (2008).
Lee, S. G. et al., "Comparison of with or without early cleavage assessment for elective single embryo transfer on day 3," Abstracts of the 26th Annual Meeting of ESHRE, P-167:i180-i181 (2010).
Lemmen et al., "Kinetic markers of human embryo quality using time-lapse recordings of IVF/ICSI-fertilized oocytes," Reprod. Biomed. Online 17:385-391 (2008).
Lequarre, et al., (2003) "Cell cycle duration at the time of maternal zygotic transition for in vitro produced bovine embryos: effect of oxygen tension and transcription inhibition," Biology of Reproduction, 69:1707-1713.
Lewin, et al. (1994) "Embryo growth rate in vitro as an indicator of embryo quality in IVF cycles," Journal of Assisted Reproduction and Genetics, 11(10):500-503.
Lewis, W.H. et al., "Cinematographs of living developing rabbit-eggs," Science, 69(1782):226-229 (1929).
Li, K. et al., "Cell population tracking and lineage construction with spatiotemporal context," Medical Image Analysis, 12:546-566 (2008).
Li, K. et al., "Online Tracking of Migrating and Proliferating Cells Imaged with Phase-Contrast Microscopy," Proceedings of the 2006 Conference on Computer Vision and Pattern Recognition Workshop, IEEE, 8 pages (2006).
Liebermann, J. et al., "Blastocyst development after vitrification of multipronuelear zygotes using the Flexipet denuding pipette," Reproductive BioMedicine Online, 4(2):146-150 (2002).
Liu, L. et al., "A reliable, noninvasive technique for spindle imaging and enucleation of mammalian oocytes," Nature Biotechnology, 18:223-225 (2000).
Loewke, K. E. et al., "In Vivo Micro-Image Mosaicing," IEEE Transactions on Biomedical Engineering, 58(1):159-171 (2011).
Loewke, K. E. et al., "Real-Time Image Mosaicing for Medical Applications," Proceedings of MMVR, 15:304-309 (2007).
Loewke, K. et al., "Real-time image mosaicing with a hand-held dual-axes confocal microscope," Proc. of SPIE, 6851:68510F-1-68510E-8 (2008).
Louvet-Vallee, S. et al., "Mitotic Spindles and Cleavage Planes Are Oriented Randomly in the Two-Cell Mouse Embryo," Current Biology, 15:464-469 (2005).
Lundin, et al., (2001) "Early embryo cleavage is a strong indicator of embryo quality in human IVF," Human Reproduction, 16(12):2652-2657.
Magli, M. C. et al., "Chromosomal abnormalities in embryos," Mol. Cell. Endocrinol., 183:S29-S34 (2001).
Marhuenda-Egea, F. C. et al., "Improving human embryos selection in IVF: non-invasive metabolomic and chemometric approach," Metabolomics, 7(2):247-256 (2011).
Massip, A. et al., "The behaviour of cow blastocyst in vitro: cinematographic and morphometric analysis," J. Anat., 134(2):399-405 (1982).
Massip, A. et al., "Time-lapse cinematographic analysis of hatching of normal and frozen-thawed cow blastocysts," J. Reprod. Fertil., 58:475-478 (1980).
Mastenbroek, S. et al., "In Vitro Fertilization with Preimplantation Genetic Screening," N. Engl. J. Med., 357(1):9-17 (2007).
Mauhin, "International Search Report," 7 pages, from PCT Application No. PCT/US2010/046343, European Patent Office, Rijswijk, The Netherlands (dated Nov. 15, 2010).
Mauhin, "Written Opinion of the International Searching Authority," 6 pages, from PCT Application No. PCT/US2010/046343, European Patent Office, Rijswijk, The Netherlands (dated Nov. 15, 2010).
McCarthy, E. K. et al., "Asymmetric spindle positioning," Current Opinion in Cell Biology, 18:79-85 (2006).
McKiernan, S. H. et al., "Timing of development is a critical parameter for predicting successful embryogenesis," Human Reproduction, 9(11):2123-2129 (1994).
Menezes, J. et al., "Video observations on human blastocyst hatching," Reprod. BioMed. Online, 7(2):217-218 (2003).
Meng et al., "Remote Monitoring and Evaluation of Early Human Embryo Development by a Robotic-Operated Culture-Imaging System," Fertil. Steril. 91(3) Supplement; p. S7 (2009).
Meseguer, M. et al., "The use of morphokinetics as a predictor of embryo implantation," Hum. Reprod., 26(10):2658-2671 (2011) [Published online Aug. 9, 2011; pp. 1-14].

(56) References Cited

OTHER PUBLICATIONS

Miles, H. L., "In Vitro Fertilization Improves Childhood Growth and Metabolism," J. Clin. Endocrinol. Metab., 92(9):3441-3445 (2007).
Milki, A. A. et al., "Accuracy of day 3 criteria for selecting the best embryos," Fertility and Sterility, 77(6):1191-1195 (2002).
Milki, A. A. et al., "Comparison of blastocyst transfer with day 3 embryo transfer in similar patient populations," Fertility and Sterility, 73(1):126-129 (2000).
Milki, A. A. et al., "Elective single blastocyst transfer," Fertility and Sterility, 81(6):1697-1698 (2004).
Mio and Maeda, "Time-lapse cinematography of dynamic changes occurring during in vitro development of human embryos," Am. J. Obstet. Gynecol. 199:660.e1-660.e5 (2008).
Mio, "Morphological analysis of human embryonic development using time-lapse cinematography," J. Mamm. Ova. Res. 23:27-35 (2006).
Mitalipov, S. M. et al., "Monozygotic Twinning in Rhesus Monkeys by Manipulation of In Vitro-Derived Embryos," Biol. Reprod., 66:1449-1455 (2002).
Montag, et al. (2008) "Symposium: Innovative techniques in human embryo viability assessment. Oocyte assessment and embryo viability prediction: birefringence imaging," Reprod. BioMed. Online, 17(4):454-460.
Montag, M. et al., "Significance of the number of embryonic cells and the state of the zona pellucida for hatching of mouse blastocysts in vitro versus in vivo," Biol. Reprod., 62:1738-1744 (2000).
Montag, M. et al., "Which morpohological scoring system is relevant in human embryo development," Placenta, 32:S252-S256 (2011).
Mottla, G. L. et al., "Lineage tracing demonstrates that blastomeres of early cleavage-stage human pre-embryos contribute to both trophectoderm and inner cell mass," Human Reproduction, 10(2):384-391 (1995).
Mtango, N. R. et al., "Oocyte Quality and Maternal Control of Development," Int. Rev. Cell. Mol. Biol., 268:223-290 (2008).
Munne, S. et al., "Improved implantation after preimplantation genetic diagnosis of aneuploidy," Reprod. Biomed. Online, 7(1):91-97 (2003).
Munne, S. et al., "Self-correction of chromosomally abnormal embryos in culture and implications for stem cell production," Fertil. Steril., 84(5):1328-1334 (2005).
Nagy, Z. P. et al., "Metabolomic assessment of oocyte viability," Reproductive BioMedicine Online,18(2):219-225 (2008).
Nagy, Z. P. et al., "Symposium: Innovative techniques in human embryo viability assessment. Non-invasive assessment of embryo viability by metabolomic profiling of culture media ('metabolomics')," Reproductive BioMedicine Online, 17(4):502-507 (2008).
Nagy, Z. P. et al., "Time-course of oocyte activation, pronucleus formation and cleavage in human oocytes fertilized by intracytoplasmic sperm injection," Human Reproduction, 9(9):1743-1748 (1994).
Nakahara, T. et al., "Evaluation of the safety of time-lapse observations for human embryos," J. Assist. Reprod. Genet., 27:93-96 (2010).
National Summary Report, The Centers for Disease Control and Prevention ("CDC") ART 2010 statistics as published on the CDC's website (2012).
Nomura, et al. (2007) "Preferable correlation to blastocyt development and pregnancy rates with a new embryo grading system specific for day 3 embryos" J. Assisted Reprod. Genet. 24:24-28.
Office Action for European Patent Application No. 10748195.4 (dated Jun. 6, 2012).
Office Action for Inter Partes Reexamination Application 95/001,785 (dated Jun. 11, 2012).
Office Action for U.S. Appl. No. 13/302,908 (dated Apr. 20, 2012).
Office Action for U.S. Appl. No. 13/302,914 (dated Apr. 26, 2012).
Ogilvie, C.M., "Review," Obstetrician & Gynaecol., 10:88-92 (2008).
Oh, S.J. et al., "Light intensity and wavelength during embryo manipulation are important factors for maintaining viability of preimplantation embryos in vitro," Fert. Steril., 88(Suppl. 2):1150-1157 (2007).
Olsen, N. H., "Morphology and Optics of Human Embryos from Light Microscopy," Ph.D. Thesis from IT University of Copenhagen; defended Mar. 24, 2003 (2003).
Opposition to EP-B-2430454, filed at the EPO on Feb. 18, 2013, 21 pages.
Ottosen, L. D. et al., "Light exposure of the ovum and preimplantation embryo during ART procedures," J. Assist. Reprod. Genet., 24:99-103 (2007).
Ottosen, L. D. et al., "Murine pre-embryo oxygen consumption and developmental competence," J. Assist. Reprod. Genet., 24:359-365 (2007).
Pantos, K. et al., "Comparison of embryo transfer on day 2, day 3, and day 6: a prospective randomized study," Fertility and Sterility, 81(2):454-455 (2004).
Park, A., "Predicting IVF Success," The Top 10 Everything of 2010, Top 10 Medical Breakthroughs, Time Magazine, Dec. 9, 2010, as published on Time Magazine's website (2012).
Payne et al., "Relationship between pre-embryo pronuclear morphology (zygote score) and standard day 2 or 3 embryo morphology with regard to assisted reproductive technique outcomes," Fertil. Steril. 84(4):900-909 (2005).
Payne, D. et al., "Preliminary observations on polar body extrusion and pronuclear formation in human oocytes using time-lapse video cinematography," Human Reproduction, 12(3):532-541 (1997).
Pedersen, U. D. et al., "A multiphase variational level set approach for modelling human embryos," ICCV Workshop on VGLSMCV (2003).
Pedersen, U. D. et al., "Modeling Human Embryos Using a Variational Level Set Approach," Ph.D. Thesis from IT University of Copenhagen (2004).
Pennetier et al., "Spatio-Temporal Expression of the Germ Cell Marker Genes MATER, ZAR1, GDF9, BMP15, and VASA in Adult Bovine Tissues, Oocytes, and Preimplantation Embryos," Biol. Reprod. 71:1359-1366 (2004).
Petersen, et al. (2001) "Embryo selection by the first cleavage parameter between 25 and 27 hours after ICSI," J. Assisted Reprod and Genetics 18(4):209-212.
Pearce, "Stanford University's patent on embryo selection is not excluded under European patent law," Reprod. BioMed. Online (2013), doi: http://dx.doi.org/10.1016/j.rbmo.2013.11.001.
Piotrowska, K. et al., "Blastomeres arising from the first cleavage division have distinguishable fates in normal mouse development," Development, 128:3739-3748 (2001).
Piotrowska, K. et al., "Early patterning of the mouse embryo—contributions of sperm and egg," Development, 129:5803-5813 (2002).
Piotrowska, K. et al., "Role the sperm in spatial patterning of the early mouse embryo," Nature, 409:517-521 (2001).
Piotrowska-Nitsche, K. et al., "Four-cell stage mouse blastomeres have different developmental properties," Development, 132:479-490 (2004).
Piotrowska-Nitsche, K. et al., "Spatial arrangement of individual 4-cell stage blastomeres and the order in which they are generated correlate with blastocyst pattern in the mouse embryo," Mechanisms of Development, 122:487-500 (2005).
Plusa, B. et al., "The first cleavage of the mouse zygote predicts the blastocyst axis," Nature, 434:391-395 (2005).
Prados, N. et al., "Improved human embryo quality in days 3 and 5 with a low oxygen closed culture system," Abstracts of the 26th Annual Meeting of ESHRE, P-191:i190 (2010).
Pribensky et al., "Prediction of in-vitro developmental competence of early cleavage-stage mouse embryos with compact time-lapse equipment," Reprod. BioMed., 20:371-379 (2010).
Qian, Y-L. et al., "Accuracy of a combined score of zygote and embryo morphology for selecting the best embryos for IVF," J. Zhejiang Univ. Sci. B, 9(8):649-655 (2008).

(56) References Cited

OTHER PUBLICATIONS

Quinlan, G. A. et al., "Lineage Allocation During Early Embryogenesis—Mapping of the Neural Primordia and Application to the Analysis of Mouse Mutants," Methods in Molecular Biology, 158:227-250 (2001).
Racowsky, C. et al., "Day 3 and day 5 morphological predictors of embryo viability," Reprod. BioMed. Online, 6(3):323-331 (2003).
Racowsky, C., "High rates of embryonic loss, yet high incidence of multiple births in human ART: is this paradoxical?", Theriogenology, 57:87-96 (2002).
Ralston, A. et al., "Cdx2 acts downstream of cell polarization to cell-autonomously promote trophectoderm fate in the early mouse embryo," Devel. Biol., 313:614-629 (2008).
Ramsing and Callesen, (2006) "Automated image analysis quantifies blastomere activity in time-lapse images to detect onset and duration of cell division during embryo development," Abstracts of the 22$^{nd}$ Annual Meeting of the ESHRE, Prague, Czech Republic, Jun. 18-21, 2006.
Ramsing, N. B. et al., "Detecting timing and duration of cell divisions by automatic image analysis may improve selection of viable embryos," Fertility and Sterility, P-153:S189 (2006).
Ramsing, N.B. et al., "Automated detection of cell division and movement in time-lapse images of developing bovine embryos can improve selection of viable embryos," Fertil. Steril., 88:S38 (2007).
Ramsing, N.B. et al., "Morphokinetic analysis of embryo development," Unisense FertiliTech, Version F7.797.4, pp. 1-15 (Nov. 16, 2011).
Ramsing, N.B. et al., "Morphokinetic analysis of embryo development," Unisense FertiliTech, Version 027, pp. 1-14 (Jun. 15, 2011).
Ramunas, J. et al., "True Monolayer Cell Culture in a Confined 3D Microenvironment Enables Lineage Informatics," Cytometry Part A, 69A:1202-1211 (2007).
Rawe, V. Y. et al., "Cytoskeletal organization defects and abortive activation in human oocytes after IVF and ISCI failure," Mol. Human. Reprod., 6:510-516 (2000).
Redacted email received by Dr. Reijo-Pera, 1 page (dated Nov. 21, 2010).
Redline comparison between "Ramsing, N.B. et al., 'Morphokinetic analysis of embryo development,' Unisense FertiliTech, Version 027, pp. 1-14 (Jun. 15, 2011)" and "Ramsing, N.B. et al., 'Morphokinetic analysis of embryo development,' Unisense FertiliTech, Version F7.797.4, pp. 1-15 (Nov. 16, 2011)," 17 pages, (2012).
Request for Inter Partes Reexamination (dated Oct. 14, 2011), Certification (dated Jun. 8, 2012) and Office Action (dated Jun. 11, 2012) for U.S. Appl. No. 95/001,785.
Response to Inter Partes Reexamination Office Action (dated Sep. 11, 2012).
Rienzi, L. et al., "Significance of morphological attributes of the early embryo," Reprod. BioMed. Online, 10(5):669-681 (2005).
Rijinders, P. M. et al., "The predictive value of day 3 embryo morphology regarding blastocyst formation, pregnancy, and implantation rate after day 5 transfer following in vitro fertilization or intracytoplasmic sperm injection," Human Reproduction, 13(10):2869-2873 (1998).
Rosenbusch, B. E., "Mechanisms giving rise to triploid zygotes during assisted reproduction," Fertility and Sterility, 90(1):49-55 (2008).
Rossant, J. et al., "Lineage allocation and asymmetries in the early mouse embryo," Phil. Tran. R. Soc. Lond., 358:1341-1348 (2003).
Safran, et al. (2000) "Blastocyst Culture in Evaluating Embryos of Reduced Quality," Reproductive Technologies, 10(3):154-157.
Sakkas, D. et al., "Early cleavage of human embryos to the two-cell stage after intracytoplasmic sperm injection as an indicator of embryo viability," Hum. Reprod., 13(1):182-187 (1998).
Salumets, et al. (2001) "The predictive value of pronuclear morphology of zygotes in the assessment of human embryo quality," Hum. Reprod. 16(10):2177-2181.
Sathananthan, A. H. et al., "Development of the human dispermic embryo," Human Reproduction Update, 5(5):553-560 (1999).
Schatten et al. (2005) "The significance of mitochondria for embryo development in cloned farm animals," Mitochondrion, 5(5):303-321.
Scott, L. et al., "Symposium: Innovative techniques in human embryo viability assessment. Human oocyte respiration-rate measurement-potential to improve oocyte and embryo selection?" Reprod. BioMed. Online, 17(4):461-469 (2008).
Seli, E. et al., "OMICS in assisted reproduction: possibilities and pitfalls," Mol. Hum. Reprod., 16(8):513-530 (2010).
Selman (1982) "Determination of the first two cleavage furrows in developing eggs of *Triturus alpestris* compared with other forms," Develop. Growth and Differ. 24(1):1-6.
Sepulveda, S. et al., "In vitro development and pregnancy outcomes for human embryos cultured in either a single medium or in a sequential media system," Fertil. Steril., 91(5):1765-1770 (2009).
Shahine, L. K. et al., "Day 2 versus day 3 embryo transfer in poor responders: a prospective randomized trial," Fertility and Sterility, 95(1):330-332 (2011).
Shen, S. et al., "Day 2 transfer improves pregnancy outcome in in vitro fertilization cycles with few available embryos," Fertility and Sterility, 86(1):44-50 (2006).
Shi, J. et al., "Good features to track," Proceedings of CVPR, pp. 593-600 (1994) (contains duplicate pages for figure clarity).
Shoukir et al., "Early cleavage of in-vitro fertilized human embryos to the 2-cell stage: a novel indicator of embryo quality and viability," Hum. Reprod. 12(7):1531-1536 (1997).
Sifer, C. et al., "An auto-controlled prospective comparison of two embryos culture media (G III series versus ISM) for IVF and ICSI treatments," J. Assist. Reprod. Genet., 26:575-581 (2009).
Squirrell, et al. (2003) "Imaging Mitochondrial Organization in Living Primate Oocytes and Embryos Using Multiphoton Microscopy," Microsc. Microanal. 9:190-201.
Squirrell, J. M. et al., "Long-term two-photon fluorescence imaging of mammalian embryos without compromising viability," Nat. Biotech., 17:763-767 (1999).
Sterckx et al., "Patenting time-lapse microscopy: the European story," Reprod. BioMed. Online (2013), doi: http://dx.doi.org/10.1016/j.rbmo.2013.09.018.
Sterckx et al., "Stanford University's patent on embryo selection should be excluded under European patent law," Reprod. BioMed. Online (2013), doi: http://dx.doi.org/10.1016/j.rbmo.2013.11.002.
Stojkovic, M. et al., "Derivation of a human blastocyst after heterologous nuclear transfer to donated oocytes," Reprod. BioMed. Online, 11(2):226-231 (2005).
Taft, R. E., "Virtues and limitations of the preimplantation mouse embryo as a model system," Theriogenology, 69:10-16 (2008).
Takenaka, M. et al., "Effects of light on development of mammalian zygotes," PNAS, 104(36):14289-14293 (2007).
Tam, P. P. L. et al., "Gene function in mouse embryogenesis: get set for gastrulation," Nature Reviews, 8:368-381 (2007).
Tam, P. P. L. et al., "The Allocation of Epiblast Cells to Ectodermal and Germ-Line Lineages is Influenced by the Position of the Cells in the Gastrulating Mouse Embryo," Devel. Biol., 178:124-132 (1996).
Tarin, J. J. et al., "Origin and ploidy of multipronuclear zygotes," Reprod. Fertil. and Devel., 11:273-279 (1999).
Tarkowski, A. K. et al., "Experiments on the development of isolated blastomeres of mouse eggs," Nature, 184:1286-1287 (1959).
Terriou, P. et al., "Relationship between even early cleavage and day 2 embryo score and assessment of their predictive value for pregnancy," Reprod. Biomed. Online, 14(3):294-299 (2007).
Third Party Observations for European Application No. 10748195.4, dated Aug. 31, 2012, 28 pages.
Third Party Requestor's comments to Patent Owner's Response (dated Oct. 11, 2012).
Tokura, et al. (1993) "Sequential observation of mitochondrial distribution in mouse oocytes and embryos," J. Assisted Reprod. And Genet. 10(6):417-426.
Trounson et al., "Maturation of human oocytes in vitro and their developmental competence," Reproduction 121:51-75 (2001).
Trounson, A., "Comparative embryo transfer in Australia," Theriogenology, 19(1):17-29 (1983).

(56) References Cited

OTHER PUBLICATIONS

Ugajin, T. et al., "Aberrant behavior of mouse embryo development after blastomere biopsy as observed through time-lapse cinematography," Fertil. Steril., 93(8):2723-2728 (2010).
Vajta, G. et al., "Rapid growth and elongation of bovine blastocysts in vitro in a three-dimensional gel system," Theriogenology, 62:1253-1263 (2004).
Van Blerkom, et al. (2001) "A microscopic and biochemical study of fragmentation phenotypes in stage appropriate human embryos," Human Reprod. 16(4):719-729.
Van Blerkom, J. et al., "Differential mitochondrial distribution in human pronuclear embryos leads to disproportionate inheritance between blastomeres: relationship to microtubular organization, ATP content and competence," Human Reproduction, 15(12):2621-2633 (2000).
Van De Velde, H. et al., "The four blastomeres of a 4-cell stage human embryo are able to develop individually into blastocysts with inner cell mass and trophectoderm," Hum. Reprod., 23(8):1742-1747 (2008).
Van Langendonckt, A. et al., "Comparison of G1.2/G2.2 and Sydney IVF cleavage/blastocyst sequential media for the culture of human embryos: a prospective, randomized, comparative study," Fertil. Steril., 76(5):1023-1031 (2001).
Van Mootfoort, et al. (2004) "Early cleavage is a valuable addition to existing embryo selection parameters: a study using single embryo transfers," Human Reprod. 19(9):2103-2108.
Van Voorhis, B. J., "In vitro fertilization," The New England Journal of Medicine, 356(4):379-386 (2007).
Vanderwall, D. K., "Early embryonic development and evaluation of equine embryo viability," Vet. Clin. North Am. Equine. Pract., 12(1):61-83 (1996) (Abstract Only).
Vanneste, E. et al., "Chromosome instability is common in human cleavage-stage embryos," Nature Medicine, 15(5):577-583 (2009).
Veeck, L. L., Atlas of the Human Oocyte and Early Conceptus, 2:121-149 (1991).
Vejlsted, M. et al., "Post-hatching development of the porcine and bovine embryo—defining criteria for expected development in vivo and in vitro," Theriogenology, 65:153-165 (2006).
Wagner et al., "Hematopoietic Progenitor Cells and Cellular Microenvironment: Behavioral and Molecular Changes upon Interaction," Stem Cells 23:1180-1191 (2005).
Wale, P. L. et al., "Time-lapse analysis of mouse embryo development in oxygen gradients," Reprod. BioMed. Onine, 21:402-410 (2010).
Weitzman et al., "Predictive value of embryo grading for embryos with known outcomes," Fertil. Steril. 93(2):658-662 (2010).
Wells, D. et al., "Association of abnormal morphology and altered gene expression in human preimplantation embryos," Fertility and Sterility, 84(2):343-355 (2005).
Wiley, L. M. et al., "Morphology of mouse egg cylinder development in vitro: a light and electron microscopic study," J. Exp. Zool., 200:389-402 (1977).
Windt, et al. (2004) "Comparative analysis of pregnancy rates after the transfer of early dividing embryos versus slower dividing embryos," Human Reprod. 19(5):1155-1162.
Wong et al., "Non-invasive imaging of human embryos before embryonic genome activation predicts development to the blastocyst stage," Nat. Biotechnol. 28:1115-1121 (2010).
Wong et al., "Non-invasive imaging of human embryos before embryonic genome activation predicts development to the blastocyst stage," Nat. Biotechnol. 28:1115-1121 (2010) supplemental data.
Written Opinion of the International Searching Authority, PCT appl. No. PCT/US2012/026328, 8 pages (dated Aug. 3, 2012).
Written Opinion of the International Searching Authority, PCT appl. No. PCT/US2013/043639, 8 pages (dated Nov. 22, 2013).
Yamagata et al., "Long-term, six-dimensional live-cell imaging for the mouse preimplantation embryo that does not affect full-term development," J. Reprod. Dev., 55(3):343-350 (2009).
Yang, X. et al., "Nuclear reprogramming of cloned embryos and its implications for therapeutic cloning," Nature Genetics, 39(3):295-302 (2007).
Yu and Omholt (1999) "Early developmental processes in the fertilised honeybee (*Apis mellifera*) oocyte," J. Insect Physiology 45:763-767.
Zernicka-Goetz, M., "First Cell fate decisions and spatial patterning in the early mouse embryo," Seminars in Cell Dev. Bio., 15:563-572 (2004).
Zernicka-Goetz, M. et al., "Making a firm decision: multifaceted regulation of cell fate in the early mouse embryo," Nature Reviews, Genetics, 10:467-477 (2009) (contains duplicate pages for figure clarity).
Zernicka-Goetz, M., "Cleavage pattern and emerging asymmetry of the mouse embryo," Nature Reviews Mol. Cell Bio., 6:919-928 (2005).
Zernicka-Goetz, M., "Patterning of the embryo: the first spatial decisions in the life of a mouse," Development, 129:815-829 (2002).
Zernicka-Goetz, M., "The first cell-fate decisions in the mouse embryo: destiny is a matter of both chance and choice," Curr. Opin. Genet. Dev. 16:406-412 (2006).
Zhang, J. Q. et al., "Reduction in exposure of human embryos outside the incubator enhances embryo quality and blastulation rate," Reprod. Biomed. Online, 20:510-515 (2010).
Zheng and Dean, "Oocyte-Specific Genes Affect Folliculogenesis, Fertilization, and Early Development," Semin. Reprod. Med. 25(4):243-251 (2007).
Zhong, X., "High-resolution 3D reconstruction of the surface of live early-stage toad embryo," Project Report, (2005).
Ziebe, et al. (1997) "Embryo morphology or cleavage stage: how to select the best embryos for transfer after in vitro fertilization," Human Reprod. 12(7):1545-1549.
Ziebe, S. et al., "FISH analysis for chromosomes 13, 16, 18, 21, 22, X and Y in all blastomeres of IVF pre-embryos from 144 randomly selected donated human oocytes and impact on pre-embryo morphology," Human Reproduction, 18(12):2575-2581 (2003).
Zimmer, C. et al., "Segmentation and Tracking of Migrating Cells in Videomicroscopy with Parametric Active Contours: A Tool for Cell-Based Drug Testing," IEEE Transactions on Medical Imaging, 21(10)1212-1221 (2002).
Zollner, K. P. et al., "Comparison of two media for sequential culture after IVF and ICSI shows no differences in pregnancy rates: a randomized trial," Med. Sci. Monit., 10:CR1-CR7 (2004).
Zucker, R. M. et al., "Confocal Laser Scanning Microscopy of Apoptosis in Organogenesis-Stage Mouse Embryos," Cytometry, 33:348-354 (1998).
Azzarello et al., (2012) "The impact of pronuclei morphology and dynamicity on live birth outcome after time-lapse culture," Human Reprod., 27(9):2649-2657.
Dobson et al., "The unique transcriptome through day 3 of human preimplantation development", Human Molecular Genetics, (2004): 13(14):1461-1470.
El-Toukhy et al., (2009) "A multi-centre randomised controlled study of pre-IVF outpatient hysteroscopy in women with recurrent IVF implantation failure: Trial of Outpatient Hysteroscopy—[TROPHY] in IVF," Reprod. Health, 6:20 (7 pages). doi: 10.1186/1742-4755-6-20. Epub Dec. 3, 2009.
Lighten et al., "Routine addition of human insulin-like growth factor-I ligand could benefit clinical in-vitro fertilization culture," Human Reproduction, 1998, 13:3144-3150.
Manipalviratn et al., "Imprinting disorders and assisted reproductive technology," Fertil Steril., Feb. 2009, 91(2):305-315.
Racowsky et al. "National collection of embryo morphology data into Society for Assisted Reproductive Technology Clinic Outcomes Reporting System: associations among day 3 cell number, fragmentation and blastomere asymmetry, and live birth rate." Fertil Steril. May 2011;95(6):1985-1989. Epub Mar. 17, 2011.
Racowsky, C., "Is there an advantage in scoring early embryos on more than one day?." Human Reproduction (2009); 24(9):2104-2113.
Annex, List of Signatories accompanying Opposition to European Patent No. 2430454 filed at the EPO on Oct. 13, 2014 (2 pages).

(56) References Cited

OTHER PUBLICATIONS

Comments by ESHRE et al. accompanying Opposition to European Patent No. 2430454 filed at the EPO on Oct. 13, 2014. (29 total; 68 pages).
Eikeland, S. N. (2013) P-507 A model to calculate Embryo Viability and Female receptivity—Paper presented on Wednesday Oct. 16, 2013—American Society for Reproductive Medicine (ASRM) Annual Meeting in Boston. Poster presentation (4 pages).
Eikeland, S. N. (2014) Declaration of Snorre Nilsen Eikeland. Sep. 15, 2014 (1 page).
Opposition to EP-B-2430454 filed at the EPO on Feb. 19, 2015 (1 page).
Opposition to EP-B-2430454 filed at the EPO on May 18, 2015 (2 pages).
Opposition to EP-B-2430454 filed at the EPO on Sep. 16, 2014 (22 pages).
Opposition to Ep-B-2430454, filed at the EPO on Oct. 11, 2013, 5 pages.
Opposition to European Patent No. 2430454 filed at the EPO on Oct. 13, 2014 (3 pages).
Patent Proprietor letter regarding EP2430454 opposition, dated Mar. 16, 2015 (1 page).
Patent Proprietor letter regarding EP2430454 opposition, dated Nov. 13, 2014 (1 page).
Patent proprietor reply to EP2430454 opposition, dated Apr. 7, 2014. (47 pages).
Society of Assisted Reproductive Technology, Clinic Summary Report 2010 (1 page).
Summons to attend EPO Oral Proceedings pursuant to Rule 115(1) EPC to patent proprieter et al., dated Mar. 19, 2015 (23 pages).
The Centers for Disease Control and Prevention—National summary report 2010 (2 pages).
Third Party Observations for European Application No. 10748195.4, dated Oct. 31, 2013, 3 pages.
Third Party Observations for European Application No. 10748195.4, dated Oct. 31, 2013, 4 pages.

\* cited by examiner

A.

B.

Abnormal
Syngamy
(AS)

ABNORMAL SYNGAMY PHENOTYPES OBSERVED WITH TIME LAPSE IMAGING FOR EARLY IDENTIFICATION OF EMBRYOS WITH LOWER DEVELOPMENT POTENTIAL

CROSS REFERENCE TO RELATED APPLICATIONS

This application claims priority to Provisional Appln. No. 61/759,598, filed Feb. 1, 2013 and U.S. Provisional Appln. No. 61/783,958, filed Mar. 14, 2013, both of which are herein incorporated by reference in their entirety.

FIELD OF THE INVENTION

This invention relates to the field of biological and clinical testing, and particularly the imaging and evaluation of zygotes/embryos from both humans and animals.

BACKGROUND OF THE INVENTION

Infertility is a common health problem that affects 10-15% of couples of reproductive-age. In the United States alone in the year 2006, approximately 140,000 cycles of in vitro fertilization (IVF) were performed (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

The understanding in the art of basic embryo development is limited as studies on human embryo biology remain challenging and often exempt from research funding. Consequently, most of the current knowledge of embryo development derives from studies of model organisms. Embryos from different species go through similar developmental stages, however, the timing varies by species. These differences and many others make it inappropriate to directly extrapolate from one species to another. (Taft, R. E. (2008) Theriogenology 69(1):10-16). The general pathways of human development, as well as the fundamental underlying molecular determinants, are unique to human embryo development. For example, in mice, embryonic transcription is activated approximately 12 hours post-fertilization, concurrent with the first cleavage division, whereas in humans embryonic gene activation (EGA) occurs on day 3, around the 8-cell stage (Bell, C. E., et al. (2008) Mol. Hum. Reprod. 14:691-701; Braude, P., et al. (1988) Nature 332:459-461; Hamatani, T. et al. (2004) Proc. Natl. Acad. Sci. 101:10326-10331; Dobson, T. et al. (2004) Human Molecular Genetics 13(14):1461-1470). In addition, the genes that are modulated in early human development are unique (Dobson, T. et al. (2004) Human Molecular Genetics 13(14):1461-1470). Moreover, in other species such as the mouse, more than 85% of embryos cultured in vitro reach the blastocyst stage, one of the first major landmarks in mammalian development, whereas cultured human embryos have an average blastocyst formation rate of approximately 30-50%, with a high incidence of mosaicism and aberrant phenotypes, such as fragmentation and developmental arrest (Rienzi, L. et al. (2005) Reprod. Biomed. Online 10:669-681; Alikani, M., et al. (2005) Mol. Hum. Reprod. 11:335-344; Keltz, M. D., et al. (2006) Fertil. Steril. 86:321-324; French, D. B., et al. (2009) Fertil. Steril.). In spite of such differences, the majority of studies of preimplantation embryo development derive from model organisms and are difficult to relate to human embryo development (Zernicka-Goetz, M. (2002) Development 129:815-829; Wang, Q., et al. (2004) Dev Cell. 6:133-144; Bell, C. E., et al. (2008) Mol. Hum. Reprod. 14:691-701; Zernicka-Goetz, M. (2006) Curr. Opin. Genet. Dev. 16:406-412; Mtango, N. R., et al. (2008) Int. Rev. Cell. Mol. Biol. 268:223-290).

Traditionally in IVF clinics, human embryo viability has been assessed by simple morphologic observations such as the presence of uniformly-sized, mononucleate blastomeres and the degree of cellular fragmentation (Rijinders P M, Jansen C A M. (1998) Hum Reprod 13:2869-73; Milki A A, et al. (2002) Fertil Steril 77:1191-5). More recently, additional methods such as extended culture of embryos (to the blastocyst stage at day 5) and analysis of chromosomal status via preimplantation genetic diagnosis (PGD) have also been used to assess embryo quality (Milki A, et al. (2000) Fertil Steril 73:126-9; Fragouli E, (2009) Fertil Steril June 21 [EPub ahead of print]; El-Toukhy T, et al. (2009) Hum Reprod 6:20; Vanneste E, et al. (2009) Nat Med 15:577-83). However, potential risks of these methods also exist in that they prolong the culture period and disrupt embryo integrity (Manipalviratn S, et al. (2009) Fertil Steril 91:305-15; Mastenbroek S, et al. (2007) N Engl J Med. 357:9-17).

U.S. Pat. Nos. 7,963,906; 8,323,177 and 8,337,387 describe novel timing parameters including the duration of the first cytokinesis, the interval between cytokinesis 1 and cytokinesis 2, the interval between mitosis 1 and mitosis 2, the interval between cytokinesis 2 and cytokinesis 3 and the interval between mitosis 2 and mitosis 3 that are useful in selecting embryos with good developmental potential that are likely to reach the blastocyst stage, implant into the uterus and/or be born live.

Not withstanding the recent developments in time lapse imaging that allow clinicians to select embryos with greater developmental potential based on timing parameters of the first few cell cycles, current embryo selection relies primarily on morphological evaluations which are very subjective and offer limited predictive value of embryo viability. Failure to correctly identify the most viable embryos can lead to unsuccessful IVF treatment or multiple gestation pregnancy. Time-lapse imaging technology allows real time embryo monitoring and provides additional insight into human embryo developmental biology. This technology has allowed for the identification of new atypical embryo phenotypes and new timing parameters that may impact embryo development including the novel syngamy parameters described herein.

SUMMARY OF THE INVENTION

The invention provides for methods, compositions and kits for determining the likelihood that one or more embryos will reach the blastocyst stage become a good quality blastocyst, or implant into the uterus or be born live or be euploid. These methods, compositions and kits are useful in methods of treating infertility in humans and other animals.

In some aspects of the invention, methods are provided for determining the likelihood that an embryo will reach the blastocyst stage and/or become a good quality blastocyst and/or implant into the uterus and/or be euploid. In some aspects determining the likelihood of reaching the blastocyst stage and/or becoming a good quality blastocyst and/or implanting into the uterus and/or be euploid is determined by deselecting with high specificity one or more human embryos that is not likely to reach the blastocyst stage, become a good quality blastocyst, or implant into the uterus, wherein at least about 70%, 75%, 80%, 85%, 90%, 95% or more or 100% of the human embryos deselected are not likely to reach the blastocyst stage and/or implant into the uterus. In such aspects, cellular parameters of an embryo are measured to arrive at a cellular parameter measurement which can be employed to provide a determination of the likelihood of the embryo to reach the blastocyst stage and or implant into a uterus, which determination may be used to guide a clinical course of action. In some embodiments, the cellular parameter is a morphological event that is measurable or observable by time-lapse microscopy. In particular embodiments, the morphological event is syngamy. In a further embodiment, the time period between syngamy and the beginning of the first cytokinesis is measured, defined as syngamy timing parameter ($P_{syn}$).

In one embodiment, embryos are monitored to determine their phenotype during syngamy. In further embodiments, embryos are deselected as being less likely to reach the blastocyst stage or develop into good quality blastocysts or implant into the uterus when syngamy is abnormal (AS). In a particular embodiment, an embryo is determined to display AS when there is disordered pronuclei (PN) movement, delayed dispersion of nuclear envelopes, active oolema movement before the dispersion of the nuclear envelopes and/or a short (e.g. less than about 2.5 hours, less than about 2 hours, less than about 1.5 hours, less than about 1 hour, less than about 30 minutes, or less than about 15 minutes) time period between syngamy and the beginning of the first cytokinesis ($P_{syn}$). Therefore, in one embodiment, the time period between syngamy and the beginning of the first cytokinesis ($P_{syn}$) is measured. In a particular embodiment, embryos with a short time period between syngamy and the first cytokinesis ($P_{syn}$) are less likely to reach the blastocyst stage or implant into the uterus and therefore are deselected. In some embodiment, embryos with a shorter time period between syngamy and the first cytokinesis ($P_{syn}$) are less likely to reach the blastocyst stage or to develop into a good quality blastocyst. These embryos show lower potential of development and may have lower potential to implant into the uterus and therefore are deselected. In some embodiments, embryos are deselected as being less likely to reach the blastocyst stage or implant into the uterus when $P_{syn}$ is immeasurable.

In some embodiments, in addition to measuring $P_{syn}$ and identifying AS or immeasurable syngamy, one or more additional cellular parameters are measured including: the duration of a cytokinesis event, e.g. the duration of cytokinesis 1, the time interval between cytokinesis 1 and cytokinesis 2; or the time interval between cytokinesis 2 and cytokinesis 3. In some embodiments, the one or more cellular parameters is: the duration of a mitotic event, e.g. the time interval between mitosis 1 and mitosis 2; and the time interval between mitosis 2 and mitosis 3. In certain embodiments, the duration of cell cycle 1 is also utilized as a cellular parameter. In certain embodiments, the time between fertilization and the 5 cell stage is also utilized as a cellular parameter. In some embodiments, the cell parameter measurement is employed by comparing it to a comparable cell parameter measurement from a reference embryo, and using the result of this comparison to provide a determination of the likelihood of the embryo to reach the blastocyst stage and/or become a good quality blastocyst and/or implant into the uterus. In some embodiments, the embryo is a human embryo.

In some aspects of the invention, methods are provided for selecting one or more human embryos that is likely to reach the blastocyst stage or become a good quality blastocyst or successfully implant into the uterus by culturing one or more human embryos under conditions sufficient for embryo development. In certain embodiments, the embryos are frozen prior to culturing. In other embodiments, the embryos are not frozen prior to culturing. In certain embodiments, the one or more human embryos are produced by fertilization of oocytes in vitro. In further embodiments, the oocytes that are fertilized in vitro are also matured in vitro and may be supplemented with growth factors. In certain embodiments, the one or more human embryos that is cultured under conditions sufficient for embryo development is further imaged by time lapse imaging for a duration sufficient to include at least one cytokinesis event or cell cycle. In a particular embodiment, the time lapse imaging acquires images that are digitally stored. In one embodiment, the time lapse imaging employs darkfield illumination. In another embodiment, the time lapse imaging employs brightfield illumination. In still a further embodiment, the time lapse imaging employs a combination of darkfield and brightfield illumination. In one embodiment, the time-lapse imaging employs single plane acquisition. In another embodiment, the time-lapse imaging employs multi-plane acquisition. In one embodiment, one or more cellular parameters is measured by time lapse microscopy. In one embodiment, the one or more cellular parameters is the duration of the first cytokinesis, the time interval between the first and second mitosis, the time interval between the second and third mitosis, the time interval between cytokinesis 1 and cytokinesis 2, the time interval between cytokinesis 2 and cytokinesis 3, the duration of the first cell cycle and the time between fertilization and the 5 cell stage. In still a further embodiment, an embryo is selected when the duration of the first cytokinesis is about 0 to about 33 minutes or the time interval between mitosis 1 and mitosis 2 is about 7.8 to about 14.3 hours, or the time interval between mitosis 2 and mitosis 3 is about 0 to about 5.8 hours or the time interval between the first cytokinesis and the second cytokinesis is about 7.8 to about 14.3 hours, or the time interval between cytokinesis 2 and cytokinesis 3 is about 0 to about 5.8 hours, or the duration of the first cell cycle is about 24 hours or the time between fertilization and the 5 cell stage is about 47 to about 57 hours. In still a further embodiment, a human embryo selected to be more likely to reach the blastocyst stage or implant into the uterus is deselected when the embryo displays AS, for example when the embryo displays disordered PN movement, delayed dispersion of nuclear envelopes, active oolema movement before the dispersion of the nuclear envelopes and/or a short (e.g. less than about 2.5 hours, less than about 2 hours, less than about 1.5 hours, less than about 1 hour, less than about 30 minutes, or less than about 15 minutes) time period between syngamy and the beginning of the first cytokinesis ($P_{syn}$), or when syngamy is immeasurable in the embryo.

In one embodiment, methods are provided to determine whether or not an embryo is likely to be euploid or aneuploid. In one embodiment, an embryo is determined to be euploid when it displays a time between syngamy and the beginning of the first cytokinesis ($P_{syn}$) that is more than about 2.4 hours, for example, more than about 2.5 hours. In a related embodiment, an embryos is determined to be aneuploid when it displays a $P_{syn}$ of less than about 2.4 hours, for example less than about 2 hours, or less than about 1.5 hours, or less than about 1 hour or less than about 30 min or less than about 15 min.

In some aspects of the invention, methods are provided to select the best embryos that are most likely to reach blastocyst stage, and/or develop into good quality blastocysts, and/or have higher potential of development and/or implant into the uterus, and/or be born live and/or be euploid, by culturing human embryos in vitro, time-lapse imaging the embryos to measure cellular parameters, employing the cellular parameters to determine the likelihood of the embryo reaching blastocyst, becoming a good quality blastocyst, implanting into the uterus and/or being born live and/or be euploid and further by deselecting embryos that fall within certain other cellular parameters that make it less likely that the one or more human embryo will reach the blastocyst stage, implant into the uterus and/or be born live and/or more likely that the embryo will be aneuploid.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
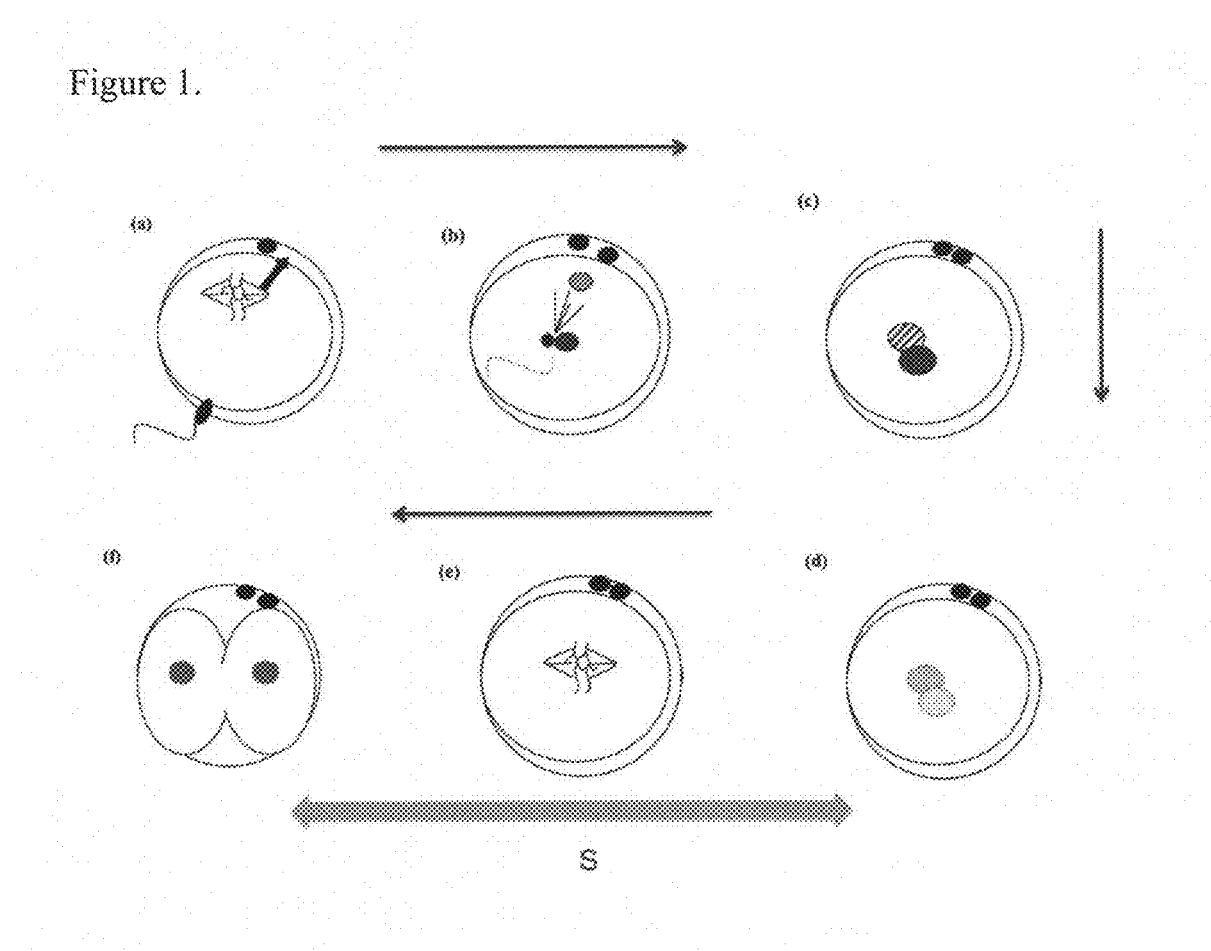
FIG. 1 is a schematic diagram depicting the series of events from fertilization to the first cell division. (a) Sperm entry into the oocyte triggers completion of meiosis. Sister chromatids separate at anaphase II, creating a haploid oocyte. (b) A second polar body is extruded, and a pronuclear envelope forms around the remaining oocyte's chromosomes to give the female pronucleus, while the sperm chromosomes decondense, forming the male pronucleus. A sperm aster sits in close proximity to the male pronucleus, from which a microtubule arrangement extends towards the female pronucleus. (c) The female pronucleus is drawn towards the male pronucleus until the two abut in the centre of the oocyte; the pronuclei significantly increase in size. (d) The pronuclear envelopes disassemble. (e) The centrioles divide to opposite poles and the chromosomes align on the first mitotic spindle at metaphase. (f) First cytokinesis start, Chromosomes segregate to two new daughter cells and the nuclear envelope forms to give the first embryonic nuclei. (S) time from the pronuclei disappearance (syngamy) (D) to first cytokinesis (f).

Before the present methods and compositions are described, it is to be understood that this invention is not limited to any particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, compositions and kits for determining the likelihood of reaching the blastocyst stage and/or implant into the uterus. These methods, compositions and kits find use in identifying embryos in vitro that are most useful in treating infertility in humans. These and other objects, advantages, and features of the invention will become apparent to those persons skilled in the art upon reading the details of the subject methods and compositions as more fully described below.

The terms "developmental potential" and "developmental competence" are used herein to refer to the ability or capacity of a healthy embryo or to grow or develop. The terms may refer to the ability or capacity of a healthy embryo to reach the blastocyst stage, or develop into a good quality blastocyst or implant into the uterus, or be born live.

The term "specificity" when used herein with respect to prediction and/or evaluation methods is used to refer to the ability to predict or evaluate an embryo for determining the likelihood that the embryo will not develop into a blastocyst by assessing, determining, identifying or selecting embryos that are not likely to reach the blastocyst stage and/or implant into the uterus. High specificity as used herein refers to where at least about 70%, 72%, 75%, 77%, 80%, 82%, 85%, 88%, 90%, 92%, 95% or more, or 100% of the human embryos not selected are not likely to reach the blastocyst stage and/or implant into the uterus and/or be euploid. In some embodiments, embryos that are not likely to reach the blastocyst stage and/or implant into the uterus or those that are likely to be aneuploid are deselected.

The term "embryo" is used herein to refer both to the zygote that is formed when two haploid gametic cells, e.g. an unfertilized secondary oocyte and a sperm cell, unite to form a diploid totipotent cell, e.g. a fertilized ovum, and to the embryo that results from the immediately subsequent cell divisions, i.e. embryonic cleavage, up through the morula, i.e. 16-cell stage and the blastocyst stage (with differentiated trophectoderm and inner cell mass).

The term "blastocyst" is used herein to describe all embryos that reach cavitation (i.e., the formation of cavities).

The terms "born live" or "live birth" are used herein to include but are not limited to healthy and/or chromosomally normal (normal number of chromosomes, normal chromosome structure, normal chromosome orientation, etc.) births.

The term "arrested" is used herein to refer to any embryo that does not meet the definition of blastocyst.

The term "oocyte" is used herein to refer to an unfertilized female germ cell, or gamete. Oocytes of the subject application may be primary oocytes, in which case they are positioned to go through or are going through meiosis I, or secondary oocytes, in which case they are positioned to go through or are going through meiosis II.

By "meiosis" it is meant the cell cycle events that result in the production of gametes. In the first meiotic cell cycle, or meiosis I, a cell's chromosomes are duplicated and partitioned into two daughter cells. These daughter cells then divide in a second meiotic cell cycle, or meiosis II, that is not accompanied by DNA synthesis, resulting in gametes with a haploid number of chromosomes.

By a "mitotic cell cycle", it is meant the events in a cell that result in the duplication of a cell's chromosomes and the division of those chromosomes and a cell's cytoplasmic matter into two daughter cells. The mitotic cell cycle is divided into two phases: interphase and mitosis. In interphase, the cell grows and replicates its DNA. In mitosis, the cell initiates and completes cell division, first partitioning its nuclear material, and then dividing its cytoplasmic material and its partitioned nuclear material (cytokinesis) into two separate cells.

By a "first mitotic cell cycle" or "cell cycle 1" or "P1" it is meant the time interval from fertilization to the completion of the first cytokinesis event or first mitosis, i.e. the division of the fertilized oocyte into two daughter cells. In instances in which oocytes are fertilized in vitro, the time interval between the injection of human chorionic gonadotropin (HCG) (usually administered prior to oocyte retrieval) to the completion of the first cytokinesis event may be used as a surrogate time interval.

By a "second mitotic cell cycle" or "cell cycle 2" or "P2" it is meant the second cell cycle event observed in an embryo, the time interval between the production of daughter cells from a fertilized oocyte by mitosis and the production of a first set of granddaughter cells from one of those daughter cells (the "leading daughter cell", or daughter cell A) by mitosis. P2 also encompasses the duration of time that the embryo is a 2 cell embryo, that is the duration of the 2 cell stage. Cell cycle 2 may be measured using several morphological events including the end of cytokinesis 1 and the beginning of cytokinesis 2, or the end of cytokinesis 1 and the end of cytokinesis 2 or the beginning of cytokinesis 1 and the beginning of cytokinesis 2 or the beginning of cytokines 1 and the end of cytokinesis 2 or the end of mitosis 1 and the beginning of mitosis 2 or the end of mitosis 1 and the end of mitosis 2 or the beginning of mitosis 1 and the beginning of mitosis 1 or the beginning of mitosis 1 and the end of mitosis 2. Upon completion of cell cycle 2, the embryo consists of 3 cells. In other words, cell cycle 2 can be visually identified as the time between the embryo containing 2-cells and the embryo containing 3-cells.

By a "third mitotic cell cycle" or "cell cycle 3" or "P3" it is meant the third cell cycle event observed in an embryo, typically the time interval from the production of a first set of granddaughter cells from a fertilized oocyte by mitosis and the production of a second set of granddaughter cells from the second daughter cell (the "lagging daughter cell" or daughter cell B) by mitosis. Cell cycle 3 may be measured using several morphological events including the end of cytokinesis 2 and the beginning of cytokinesis 3, or the end of cytokinesis 2 and the end of cytokinesis 3 or the beginning of cytokinesis 2 and the beginning of cytokinesis 3 or the beginning of cytokinesis 2 and the end of cytokinesis 3 or the end of mitosis 3 and the beginning of mitosis 3 or the end of mitosis 2 and the end of mitosis 3 or the beginning of mitosis 2 and the beginning of mitosis 3 or the beginning of mitosis 2 and the end of mitosis 3. In other words, cell cycle 3 can be visually identified as the time between the embryo containing 3-cells and the embryo containing 4-cells.

By "first cleavage event" or "first cleavage", it is meant the first division, i.e. the division of the oocyte into two daughter cells, i.e. cell cycle 1. Upon completion of the first cleavage event, the embryo consists of 2 cells.

By "second cleavage event" or "second cleavage", it is meant the second set of divisions, i.e. the division of leading daughter cell into two granddaughter cells and the division of the lagging daughter cell into two granddaughter cells. In other words, the second cleavage event consists of both cell cycle 2 and cell cycle 3. Upon completion of second cleavage, the embryo consists of 4 cells.

By "third cleavage event", it is meant the third set of divisions, i.e. the divisions of all of the granddaughter cells. Upon completion of the third cleavage event, the embryo typically consists of 8 cells.

By "cytokinesis" or "cell division" it is meant that phase of mitosis in which a cell undergoes cell division. In other words, it is the stage of mitosis in which a cell's partitioned nuclear material and its cytoplasmic material are divided to produce two daughter cells. The period of cytokinesis is identifiable as the period, or window, of time between when a constriction of the cell membrane (a "cleavage furrow") is first observed and the resolution of that constriction event, i.e. the generation of two daughter cells. The initiation of the cleavage furrow may be visually identified as the point in which the curvature of the cell membrane changes from convex (rounded outward) to concave (curved inward with a dent or indentation). This is illustrated for example in FIG. 4 of U.S. Pat. No. 7,963,906 top panel by white arrows pointing at 2 cleavage furrows. The onset of cell elongation may also be used to mark the onset of cytokinesis, in which case the period of cytokinesis is defined as the period of time between the onset of cell elongation and the resolution of the cell division.

By "first cytokinesis" or "cytokinesis 1" it is meant the first cell division event after fertilization, i.e. the division of a fertilized oocyte to produce two daughter cells. First cytokinesis usually occurs about one day after fertilization.

By "second cytokinesis" or "cytokinesis 2", it is meant the second cell division event observed in an embryo, i.e. the division of a daughter cell of the fertilized oocyte (the "leading daughter cell", or daughter A) into a first set of two granddaughters.

By "third cytokinesis" or "cytokinesis 3", it is meant the third cell division event observed in an embryo, i.e. the division of the other daughter of the fertilized oocyte (the "lagging daughter cell", or daughter B) into a second set of two granddaughters.

The term "fiduciary marker" or "fiducial marker," is an object used in the field of view of an imaging system which appears in the image produced, for use as a point of reference or a measure. It may be either something placed into or on the imaging subject, or a mark or set of marks in the reticle of an optical instrument.

The term "micro-well" refers to a container that is sized on a cellular scale, preferably to provide for accommodating eukaryotic cells or a single oocyte or embryo.

The term "selecting" or "selection" refers to any method known in the art for moving one or more embryos, blastocysts or other cell or cells as described herein from one location to another location. This can include but is not limited to moving one or more embryos, blastocysts or other cell or cells within a well, dish or other compartment or device so as to separate the selected one or more embryos, blastocysts or other cell or cells of the invention from the non- or deselected one or more embryos of the invention (such as for example moving from one area of a well, dish, compartment or device to another area of a well, dish, compartment or device). This can also include moving one or more embryos, blastocysts or other cell or cells from one well, dish, compartment or device to another well, dish, compartment or device. Any means known in the art for separating or distinguishing the selected one or more embryos, blastocysts or other cell or cells from the non- or deselected one or more embryos, blastocysts or other cell or cells can be employed with the methods of the present invention. In one embodiment, selected embryos are selected for transfer to a recipient for gestation. In another embodiment, selected embryos are selected for freezing for potential future implantation. In another embodiment, embryos are selected for continued culture. In another embodiment, embryos are selected for further evaluation by other methods such as preimplantation genetic testing, genomics, proteonomics, and/or secretomics.

The term "deselected" or "deselection" as used herein refers to embryos with poor developmental potential which not chosen for implantation or are chosen for non-implantation. In some embodiments, deselected embryos are not transferred or implanted into the uterus.

After fertilization both gametes contribute one set of chromosomes (haploid content), each contained in a structured referred to herein as a "pronucleus." After normal fertilization, each embryo shows two pronuclei (PN), one representing the paternal genetic material and one representing the maternal genetic material. "Syngamy" as used herein refers to the breakdown or disappearance of the pronuclei (PN) when the two sets of chromosomes unite, occurring within a couple hours before the first cytokinesis.

The time parameter "$P_{syn}$" or "S" or "$P_{M1}$", as used interchangeably herein, refers to a parameter defined by the time from syngamy to the beginning of the first cytokinesis (i.e., the appearance of the first cytokinetic cleavage furrow). Sometimes it is not possible to visualize PN or to measure syngamy, such embryos are said to have "immeasurable syngamy" or "US" or "unmeasurable syngamy" (all terms are used interchangeably). Additionally, it is possible that an embryo will show atypical syngamy patterns or timing. Such embryos are said to have "atypical syngamy" or "abnormal syngamy" or "AS" (all three terms are used interchangeably). AS embryos show disordered PN movement within the cytoplasm without prompt dispersion of nuclear envelopes and typically have a shorter $P_{syn}$, when compared to normal syngamy or "NS" embryos. This may be visualized by time lapse microscopy when the PN move unsteadily within the cytoplasm either together or separately before their disappearance. AS embryos often also show active oolema movement before the dispersion of the nuclear envelopes. NS embryos on the other hand, show timely disappearance of PN with a smooth dispersion of the nuclear envelopes with minimal or no pronuclear movement within the cytoplasm and minimal or no oolema movement prior to the dispersion of nuclear envelopes.

The term "euploid" is used herein to refer to a cell that contains an integral multiple of the haploid, or monoploid, number. For example, a human autosomal cell having 46 chromosomes is euploid, and a human gamete having 23 chromosomes is euploid. By "euploid embryo" it is meant that the cells of the embryo are euploid.

The term "aneuploid" is used herein to refer to a cell that contains an abnormal number of chromosomes. For example, a cell having an additional chromosome and a cell missing a chromosome are both aneuploid. By "aneuploid embryo" it is meant that one or more cells of an embryo are aneuploid.

The focus of prior patents and applications including U.S. Pat. Nos. 7,963,906; 8,323,177; 8,337,387 and PCT Appl. No. WO 2012/163363 each center primarily around selection criteria for human embryos in in vitro fertilization. While these patents/applications each discuss determining whether embryos are good or poor, the timing parameters described therein are typically used in the clinic in large part to select embryos with good developmental potential. In contrast, the methods of the current invention center around three novel parameters, US, AS and $P_{syn}$, that may be used to deselect human embryos and target them for non-transfer in in vitro fertilization treatment. Alternatively, the novel parameters NS and $P_{syn}$ may be used to select human embryos for transfer into the uterus. These parameters may be used alone or in combination with the selection parameters described in U.S. Pat. Nos. 7,963,906; 8,323,177; 8,337,387 and PCT Appl. No. WO 2012/163363. For example, once an embryo is determined to have good developmental potential by the methods of U.S. Pat. Nos. 7,963,906; 8,323,177; 8,337,387 and PCT Appl. No. WO 2012/163363, that embryo may be further analyzed for the syngamy parameters described herein to further increase the sensitivity and specificity of the claimed methods.

The deselection criteria of the current invention include: AS, an atypical embryo phenotype involving pronuclear behavior that can be measured during the physiological process called syngamy, embryos exhibiting this type of phenotype are considered to have abnormal syngamy; immeasurable syngamy, an atypical embryo phenotype identified by non-visualization of the pronuclei; and $P_{syn}$, a timing parameter defined by the time from syngamy to the first cytokinesis.

Figure 2:
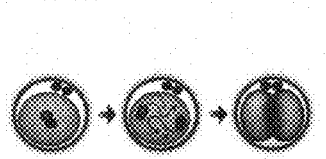
FIG. 2 (A) describes and illustrates the definition of AS and the prevalence of AS and immeasurable syngamy. (B) depicts an individual still image from a key time point during the dynamic syngamy event.
Figure 2:
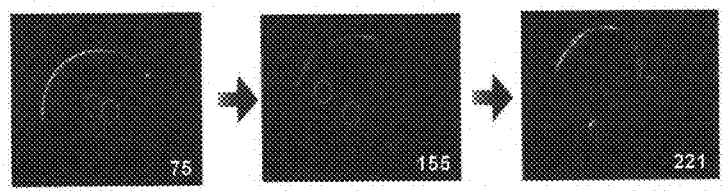

The current invention involves two specific atypical phenotypes, abnormal syngamy (AS) and immeasurable syngamy; as well as a new timing parameter, the time from syngamy to the first cytokinesis ($P_{syn}$). AS embryos have an average shorter time from syngamy to the first cytokinesis ($P_{syn}$) when compared with embryos with normal syngamy (NS) (FIGS. 1 and 2). AS embryos also show disordered PN movement within the cytoplasm without prompt dispersion of nuclear envelopes. (FIGS. 1 and 2). Therefore, AS can also be measured by evaluating the movement of pronuclei and/or pronuclei activity throughout the cytoplasm. Normal syngamy on the other hand, is characterized by a timely disappearance of pronuclei with smooth dispersion of the nuclear envelopes. In addition, to the use of AS and immeasurable syngamy as deselection criteria, NS may be used independently as a positive selection criteria. Furthermore, embryos exhibiting AS and immeasurable syngamy are less likely to have good morphology at cleavage stage (day 3), less likely to become good quality blastocysts and less likely to implant into the uterus and may be less likely to be euploid.

Additionally, a longer $P_{syn}$ indicates the daughter cells are more likely to be euploid. In contrast, a shorter $P_{syn}$ indicates the daughter cells are more likely to be aneuploid. Because embryos with AS and immeasurable syngamy have lower development potential, it is beneficial to use AS and immeasurable syngamy to deselect before embryo transfer or freezing. Importantly, any one of these three parameters, AS, immeasurable syngamy and $P_{syn}$ may be used alone or in combination with each other or other cellular parameters including the parameters included in Table 1.

TABLE 1

List of Parameters

| Parameter | Description/Reference describing Parameter |
|---|---|
| P1 | Duration of $1^{st}$ cytokinesis |
| P2 | Interval between $1^{st}$ and $2^{nd}$ cytokinesis (time from 2-cell embryo to 3-cell embryo) (end of $1^{st}$ cytokinesis to end of $2^{nd}$ cytokinesis) (duration as 2 cell embryo) (t3-t2) |
| P3 | Interval between $2^{nd}$ and $3^{rd}$ cytokinesis (time from 3-cell embryo to 4-cell embryo) (end of $2^{nd}$ cytokinesis to end of $3^{rd}$ cytokinesis) (duration as 3 cell embryo) (t4-t3) (synchrony between 3 and 4 cells) |
| $P_{syn}$ or S or $P_{M1}$ | Time from syngamy to $1^{st}$ cytokinesis |
| 2ce-3C | End of $1^{st}$ cleavage to beginning of second cleavage |
| 3C-4C | Beginning of $2^{nd}$ Cleavage to end of $3^{rd}$ Cleavage |
| t5 | Time from ICSI (fertilization) to 5 cell embryo |
| 2Cb | Time from fertilization to beginning of $1^{st}$ cleavage |
| 2Ce | Time from fertilization until end of $1^{st}$ cleavage |
| 3C | Time from fertilization to beginning of $2^{nd}$ cleavage |
| 4C | Time from fertilization to end of $3^{rd}$ cleavage |
| 5C | Time from fertilization to beginning of $4^{th}$ cleavage |
| BL | Formation of blastocoel |
| tM | Time from fertilization to morula |
| S3 | Time from 5 cell embryo to 8 cell embryo |
| t2 | Time from fertilization to 2 cell embryo |
| t3 | Time from fertilization to 3 cell embryo |
| t4 | Time from fertilization to 4 cell embryo |
| cc3 | T5-t3: Third cell cycle, duration of period as 3 and 4 cell embryo |
| t5-t2 | Time to 5 cell embryo minus time to 2 cell embryo |
| cc3/cc2 | Ratio of duration of cell cycle 3 to duration of cell cycle 2 |
| Time till first cleavage | Duration of $1^{st}$ cell cycle |
| 2PB Extrusion | Time from fertilization until the second polar body is extruded |
| PN fading | Time from fertilization until pronuclei disappear, OR time between the appearance of pronuclei appearing and pronuclei disappearing |
| tSB | Time from fertilization to the start of blastulation |
| tSC | Time from fertilization to the start of compaction |
| PN appearance | Time from fertilization until pronuclei appear |
| t6 | Time from fertilization to 6 cell embryo |
| t7 | Time from fertilization to 7 cell embryo |
| t8 | Time from fertilization to 8 cell embryo |
| cc2b | t4-t2; Second cell cycle for both blastomeres, duration of period as 2 and 3 cell blastomere embryo |
| cc2_3 | t5-t2; Second and third cell cycle, duration of period as 2, 3, and 4 blastomere embryo |
| cc4 | t9-t5; fourth cell cycle; duration of period as 5, 6, 7 and 8 blastomere embryo. |
| s3a | t6-t5; Duration of the individual cell divisions involved in the development from 4 blastomere embryo to 8 blastomere embryo |
| s3b | t7-t6; Duration of the individual cell divisions involved in the development from 4 blastomere embryo to 8 blastomere embryo |
| s3c | t8-t7; Duration of the individual cell divisions involved in the development from 4 blastomere embryo to 8 blastomere embryo |
| cc2/cc3 | WO 2012/163363 |
| cc2/cc2_3 | WO 2012/163363 |
| cc3/t5 | WO 2012/163363 |
| s2/cc2 | WO 2012/163363 |
| s3/cc3 | WO 2012/163363 |
| AC1 | Cleavage directly from 1 cell embryo to 3 or more cell embryo |
| AC2 | Cleavage of a daughter cell into more than 2 blastomeres |
| AS | Abnormal syngamy Disordered PN movement within the cytoplasm without prompt dispersion of nuclear envelopes, short time period between syngamy and the beginning of the first cytokinesis ($P_{syn}$), and/or active oolema movement before the dispersion of the nuclear envelopes. Measurable by evaluating the movement of pronuclei and/or pronuclei activity throughout the cytoplasm. |

TABLE 1-continued

List of Parameters

| Parameter | Description/Reference describing Parameter |
| --- | --- |
| MN2 | Multinucleation observed at 2 blastomere stage |
| MN4 | Multinucleation observed at 4 blastomere stage |
| EV2 | Evenness of the blastomeres in the 2 blastomere embryo |
| Mul | Multinucleation |
| Uneven or UBS | Uneven sizes of blastomeres at 2-4 cells |
| Frg | Fragmentation |
| Nec | Blastomere necrosis |
| Vac | Vacuolization |

Previous reports have investigated the time from insemination to pronuclei disappearance, also known as pronuclei breakdown (PNB) or pronuclear fading (PNF), (Basile, et al. (2013) "Type of Culture Media Does Not Affect Embryo Kinetics: A Time-Lapse Analysis of Sibling Oocytes," Human Reprod., 28(3):634-41; Azzarello, et al. (2012) "The Impact of Procuclei Morphology and Dynamicity on Live Birth Outcome After Time-Lapse Culture," Human Reprod., 27(9):2649-57; Lemmen, et al. (2008) "Kinetic Markers of Human Embryo Quality Using Time-Lapse Recordings of IVF/ICSI-Fertilize Oocytes," Reprod. Biomed. Online, 17(3):385-91). Some methods of the current invention, in contrast, are related to the timing from PN disappearance to the first cytokinesis, $P_{syn}$. Unlike the previously described parameters, $P_{syn}$ is a more reliable measurement since it does not rely on the time of insemination. Time of insemination can be imprecise, especially for eggs inseminated under classic in vitro fertilization techniques.

The methods of the current invention, therefore, provide for novel selection or deselection cellular parameters for human embryos that can be measured by time lapse microscopy.

In methods of the invention, one or more embryos is assessed for its likelihood to reach the blastocyst stage and/or become a good quality blastocyst and/or implant into the uterus and/or be euploid by measuring one or more cellular parameters of the embryo(s) and employing these measurements to determine the likelihood that the embryo(s) will reach the blastocyst stage or implant into the uterus or be euploid. Such parameters have been described, for example, in U.S. Pat. Nos. 7,963,906; 8,323,177, and 8,337,387 and PCT Appl. No.: WO 2012/163363, the disclosure of each of which is incorporated herein by reference. The information thus derived may be used to guide clinical decisions, e.g. whether or not to transfer an in vitro fertilized embryo, whether or not to transplant a cultured cell or cells, whether or not to freeze an embryo for later implantation, whether or not to continue to culture the embryo, or whether or not to evaluate the embryo by other methods such as preimplantation genetic testing, genomics, proteonomics, and/or secretomics.

Examples of embryos that may be assessed by the methods of the invention include 1-cell embryos (also referred to as zygotes), 2-cell embryos, 3-cell embryos, 4-cell embryos, 5-cell embryos, 6-cell embryos, 8-cell embryos, etc. typically up to and including 16-cell embryos, morulas, and blastocysts, any of which may be derived by any convenient manner, e.g. from an oocyte that has matured in vivo or from an oocyte that has matured in vitro.

Embryos may be derived from any organism, e.g. any mammalian species, e.g. human, primate, equine, bovine, porcine, canine, feline, etc. Preferably, they are derived from a human. They may be previously frozen, e.g. embryos cryopreserved at the 1-cell stage and then thawed. Alternatively, they may be freshly prepared, e.g., embryos that are freshly prepared (not frozen prior to culturing) from oocytes by in vitro fertilization techniques (fresh or previously frozen oocytes); oocytes that are freshly harvested and/or freshly matured through in vitro maturation techniques (including, e.g., oocytes that are harvested from in vitro ovarian tissue). They may be cultured under any convenient conditions (including different types of culture media) known in the art to promote survival, growth, and/or development of the sample to be assessed, e.g. for embryos, under conditions such as those used in the art of in vitro fertilization; see, e.g., U.S. Pat. No. 6,610,543, U.S. Pat. No. 6,130,086, U.S. Pat. No. 5,837,543, the disclosures of which are incorporated herein by reference; for oocytes, under conditions such as those used in the art to promote oocyte maturation; see, e.g., U.S. Pat. No. 5,882,928 and U.S. Pat. No. 6,281,013, the disclosures of which are incorporated herein by reference; for stem cells under conditions such as those used in the art to promote maintenance, differentiation, and proliferation, see, e.g. U.S. Pat. No. 6,777,233, U.S. Pat. No. 7,037,892, U.S. Pat. No. 7,029,913, U.S. Pat. No. 5,843,780, and U.S. Pat. No. 6,200,806, US Application No. 2009/0047263; US Application No. 2009/0068742, the disclosures of which are incorporated herein by reference. Often, the embryos are cultured in a commercially available medium such as KnockOut DMEM, DMEM-F12, or Iscoves Modified Dulbecco's Medium that has been supplemented with serum or serum substitute, amino acids, growth factors and hormones tailored to the needs of the particular embryo being assessed.

In some embodiments, the embryos are assessed by measuring cell parameters by time-lapse imaging. The embryos may be cultured in standard culture dishes. Alternatively, the embryos may be cultured in custom culture dishes, e.g. custom culture dishes with optical quality micro-wells as described herein. In such custom culture dishes, each micro-well holds a single fertilized egg or embryo, and the bottom surface of each micro-well has an optical quality finish such that the entire group of embryos within a single dish can be imaged simultaneously by a single miniature microscope with sufficient resolution to follow the cell mitosis processes. The entire group of micro-wells shares the same media drop in the culture dish, and can also include an outer wall positioned around the micro-wells for stabilizing the media drop, as well as fiducial markers placed near the micro-wells. The media drops can have different volumes. The hydrophobicity of the surface can be adjusted with plasma etching or another treatment to prevent bubbles from forming in the micro-wells when filled with media. Regardless of whether a standard culture dish or a custom culture dish is utilized, during culture, one or more developing embryos may be cultured in the same culture medium, e.g. between 1 and 30 embryos may be cultured per dish.

Images are acquired over time, and are then analyzed to arrive at measurements of the one or more cellular parameters. Time-lapse imaging may be performed with any computer-controlled microscope that is equipped for digital image storage and analysis, for example, inverted microscopes equipped with heated stages and incubation chambers, or custom built miniature microscope arrays that fit inside a conventional incubator. The array of miniature microscopes enables the concurrent culture of multiple dishes of samples in the same incubator, and is scalable to accommodate multiple channels with no limitations on the minimum time interval between successive image capture. Using multiple microscopes eliminates the need to move the sample, which improves the system accuracy and overall system reliability. The individual microscopes in the incubator can be partially or fully isolated, providing each culture dish with its own controlled environment. This allows dishes to be transferred to and from the imaging stations without disturbing the environment of the other samples.

The imaging system for time-lapse imaging may employ brightfield illumination, darkfield illumination, phase contrast, Hoffman modulation contrast, differential interference contrast, polarized light, fluorescence or combinations thereof. In some embodiments, darkfield illumination may be used to provide enhanced image contrast for subsequent feature extraction and image analysis. In addition, red or near-infrared light sources may be used to reduce phototoxicity and improve the contrast ratio between cell membranes and the inner portion of the cells.

Images that are acquired may be stored either on a continuous basis, as in live video, or on an intermittent basis, as in time lapse photography, where a subject is repeatedly imaged in a still picture. Preferably, the time interval between images should be between 1 to 30 minutes, or between 1 to 20 minutes or between 1 to 15 minutes, or between 1 to 10 minutes or between 1 to 5 minutes in order to capture significant morphological events as described below. In an alternative embodiment, the time interval between images could be varied depending on the amount of cell activity. For example, during active periods images could be taken as often as every few seconds or every minute, while during inactive periods images could be taken every 10 or 15 minutes or longer. Real-time image analysis on the captured images could be used to detect when and how to vary the time intervals. In our methods, the total amount of light received by the samples is estimated to be equivalent to approximately 52 seconds of continuous low-level light exposure for 5-days of imaging. The light intensity for a time-lapse imaging systems is significantly lower than the light intensity typically used on an assisted reproduction microscope due to the low-power of the LEDs (for example, using a 1 W LED compared to a typical 100 W Halogen bulb) and high sensitivity of the camera sensor. Thus, the total amount of light energy received by an embryo using the time-lapse imaging system is comparable to or less than the amount of energy received during routine handling at an IVF clinic. In addition, exposure time can be significantly shortened to reduce the total amount of light exposure to the embryo. For 2-days of imaging, with images captured every 5 minutes at 0.5 seconds of light exposure per image, the total amount of low-level light exposure is less than 21 seconds.

Following image acquisition, the images are extracted and analyzed for different cellular parameters, for example, zygote size, blastomeres size thickness of the zona pellucida, degree of fragmentation, symmetry of daughter cells resulting from a cell division, time intervals between the first few mitoses, duration of cytokinesis and timing and quality of syngamy. The systems and methods, including classification, tracking and imaging modalities described in Patent Appln. Nos. PCT/US2011/053537; 61/785,170; 61/785,179; 61/785,199; 61/785,216; 61/770,998 and/or 61/771,000 may be used to observe and/or measure the cellular parameters of the current invention. The disclosures of each of these applications are herein specifically incorporated by reference in their entireties.

Cellular parameters that may be measured by time-lapse imaging are usually morphological events. For example, in assessing embryos, time-lapse imaging may be used to visualize syngamy, particularly the timing of syngamy including the time between syngamy and the onset or resolution of cytokinesis 1, cytokinesis 2, cytokinesis 3, cytokinesis 4, or cytokinesis 5 or the time between syngamy and the onset or resolution of mitosis 1, mitosis 2, mitosis 3, mitosis 4, or mitosis 5. Additionally, time-lapse imaging may be used to measure the duration of a cytokinesis event, e.g. cytokinesis 1, cytokinesis 2, cytokinesis 3, cytokinesis 4, cytokinesis 5 or combinations and/or ratios of these events where the duration of a cytokinesis event is defined as the time interval between the first observation of a cleavage furrow (the initiation of cytokinesis) and the resolution of the cleavage furrow into two daughter cells (i.e. the production of two daughter cells). Another parameter of interest is the duration of a cell cycle event, e.g. cell cycle 1, cell cycle 2, cell cycle 3, cell cycle 4, cell cycle 5 or combinations and/or ratios of these events where the duration of a cell cycle event is defined as the time interval between the production of a cell (for cell cycle 1, the fertilization of an ovum; for later cell cycles, at the resolution of cytokinesis) and the production of two daughter cells from that cell. Other cellular parameters of interest that can be measured by time-lapse imaging include time intervals that are defined by these cellular events, e.g. (a) the time interval between cytokinesis 1 and cytokinesis 2, definable as any one of the interval between initiation of cytokinesis 1 and the initiation of cytokinesis 2, the interval between the resolution of cytokinesis 1 and the resolution of cytokinesis 2, the interval between the initiation of cytokinesis 1 and the resolution of cytokinesis 2; or the interval between the resolution of cytokinesis 1 and the initiation of cytokinesis 2; or (b) the time interval between cytokinesis 2 and cytokinesis 3, definable as any one of the interval between the initiation of cytokinesis 2 and the initiation of cytokinesis 3, or the interval between resolution of the cytokinesis 2 and the resolution of cytokinesis 3, or the interval between initiation of cytokinesis 2 and the resolution of cytokinesis 3, or the interval between resolution of cytokinesis 2 and the initiation of cytokinesis 3; (c) the time interval between mitosis 1 and mitosis 2, definable as any one of the interval between initiation of mitosis 1 and the initiation of mitosis 2, the interval between the resolution of mitosis 1 and the resolution of mitosis 2, the interval between the initiation of mitosis 1 and the resolution of mitosis 2; or the interval between the resolution of mitosis 1 and the initiation of mitosis 2; or (b) the time interval between mitosis 2 and mitosis 3, definable as any one of the interval between the initiation of mitosis 2 and the initiation of mitosis 3, or the interval between resolution of the mitosis 2 and the resolution of mitosis 3, or the interval between initiation of mitosis 2 and the resolution of mitosis 3, or the interval between resolution of mitosis 2 and the initiation of mitosis 3.

For the purposes of in vitro fertilization, it is considered advantageous that the embryo be transferred to the uterus early in development, e.g. by day 2 or by day 3, i.e. up through the 8-cell stage, to reduce embryo loss due to disadvantages of culture conditions relative to the in vitro environment, and to reduce potential adverse outcomes associated with epigenetic errors that may occur during culturing (Katari et al. (2009) Hum Mol Genet. 18(20):3769-78; Sepúlveda et al. (2009) Feral Steril. 91(5):1765-70). Accordingly, it is preferable that the measurement of cellular parameters take place within 2 days of fertilization, although longer periods of analysis, e.g. about 36 hours, about 54 hours, about 60 hours, about 72 hours, about 84 hours, about 96 hours, or more, are also contemplated by the present methods.

Parameters can be measured manually, or they may be measured automatically, e.g. by image analysis software. When image analysis software is employed, image analysis algorithms may be used that employ a probabilistic model estimation technique based on sequential Monte Carlo method, e.g. generating distributions of hypothesized embryo models, simulating images based on a simple optical model, and comparing these simulations to the observed image data. When such probabilistic model estimations are employed, cells may be modeled as any appropriate shape, e.g. as collections of ellipses in 2D space, collections of ellipsoids in 3D space, and the like. To deal with occlusions and depth ambiguities, the method can enforce geometrical constraints that correspond to expected physical behavior. To improve robustness, images can be captured at one or more focal planes.

Once cell parameter measurements have been obtained, the measurements are employed to determine the likelihood that the embryo will develop into a blastocyst and/or become a good quality blastocyst and/or implant into the uterus and/or be euploid or aneuploid.

In some embodiments, the cell parameter measurement is used directly to determine the likelihood that an embryo will reach the blastocyst stage or will become a good quality embryo and/or be born live and/or be aneuploid. In other words, the absolute value of the measurement itself is sufficient to determine the likelihood that an embryo will reach the blastocyst stage and/or implant into the uterus and/or be born live and/or be euploid. Examples of this in embodiments using time-lapse imaging to measure cellular parameters include, without limitation, the following, which in combination are indicative of the likelihood that an embryo will reach the blastocyst stage and/or implant into the uterus and/or be born live and/or be euploid: (a) a duration of cytokinesis that is about 0 to about 33 hours; (b) a time interval between the resolution of cytokinesis 1 and the onset of cytokinesis 2 that is about 8-15 hours, e.g. about 9-14 hours, about 9-13 hours, about 9-12 hours, or about 9-11.5 hours, or about 9.33-11.45 hours; and (c) a time interval, i.e. synchronicity, between the initiation of cytokinesis 2 and the initiation of cytokinesis 3 that is about 0-6 hours, about 0-5 hours, e.g. about 0-4 hours, about 0-3 hours, about 0-2 hours, or about 0-1.75 hours, or about 0-1.73 hours. In some embodiments, determining the likelihood that the embryo will reach the blastocyst stage and/or successfully implant into the uterus and/or be born live and/or be euploid can additionally include measuring cellular parameters, including but not limited to: a cell cycle 1 that lasts about 20-27 hours, e.g. about 25-27 hours, time from fertilization to the 5 cell stage that is about 47 hours to about 57 hours, and a duration of $P_{syn}$ that is more than about 1 hour, for example, more than about 90 minutes, or more than about 2 hours, or more than about 2.3 hours, or more than about 2.4 hours or more than about 2.5 hours.

Examples of direct measurements, any of which alone or in combination are indicative of the likelihood that an embryo will not reach the blastocyst stage and/or implant into the uterus, and/or will be aneuploid include without limitation: (a) a duration of cytokinesis 1 that is more than about 33 minutes, e.g. more than about 35, 40, 45, 50, or 60 minutes; (b) a time interval between the resolution of cytokinesis 1 and the onset of cytokinesis 2 that lasts more than 15 hour, e.g. about 16, 17, 18, 19, or 20 or more hours, or less than 8 hours, e.g. about 7, 5, 4, or 3 or fewer hours; or (c) a time interval between the initiation of cytokinesis 2 and the initiation of cytokinesis 3 that is 6, 7, 8, 9, or 10 or more hours. In some embodiments, determining the likelihood that the embryo will not reach the blastocyst stage and/or implant into the uterus and/or will be aneuploid can include additionally measuring cellular parameters, including but not limited to: a cell cycle 1 that lasts longer than about 27 hours, e.g. 28, 29, or 30 or more hours, a time interval between fertilization and the 5 cell stage that is less than about 47 hour or more than about 57 hours or a duration of $P_{syn}$ that is less than about 1 hour. For example, less than about 50 minutes, or less than about 45 minutes, or less than about 40 minutes, or less than about 35 minutes, or less than about 30 minutes, or less than about 25 minutes, or less than about 20 minutes, or less than about 15 minutes, or less than about 10 minutes, or less than about 5 minutes.

In a preferred embodiment, the methods provide for direct determination of an embryo's syngamy phenotype (i.e. AS, NS, immeasurable syngamy) which alone or in combination with the above identified cellular parameters is indicative of the likelihood that an embryo will not reach the blastocyst stage, and/or become a good quality blastocyst and/or implant into the uterus and/or will be aneuploid. For example, embryos determined to be AS, for example those that display disordered PN movement in the cytoplasm without prompt dispersion of nuclear envelopes, active oolema movement prior to the dispersion of the nuclear envelopes and/or a time period from syngamy to cytokinesis 1 that is shorter than about 120 minutes or 90 minutes, or shorter than about 1 hour or shorter than about 45 minutes or shorter than about 30 minutes are less likely to reach the blastocyst stage or implant into the uterus. Similarly, embryos that display abnormal syngamy (AS) or immeasurable syngamy are also less likely to reach blastocyst stage, and/or become good quality blastocysts and/or implant into the uterus and/or are more likely to be aneuploid.

Embryos that are aneuploid are also less likely to reach the blastocyst stage, and/or become good quality blastocysts, and/or implant into the uterus, and/or result in a live birth. In one embodiment, the methods provide for direct measurement of the time period from syngamy to cytokinesis 1 ($P_{syn}$) which alone or in combination with the above identified cellular parameters and/or syngamy phenotypes is indicative of the likelihood that an embryo will not be euploid. For example, embryos that have a $P_{syn}$ that is shorter than about 2.4 hours, or shorter than about 2.3 hours, or shorter than about 2.2 hours, or shorter than about 2.1 hours or shorter than about 2 hours, or shorter than about 1.8 hours, or shorter than about 1.6 hours are less likely to be euploid and are more likely to be aneuploid. Conversely, embryos that have a $P_{syn}$ that is 2.4 hours or longer, longer than about 2.5 hours, or longer than about 3 hours are less likely to be aneuploid and more likely to be euploid.

In some embodiments, the cell parameter measurement is employed by comparing it to a cell parameter measurement from a reference, or control, embryo, and using the result of this comparison to provide a determination of the likelihood of the embryo to reach or not reach the blastocyst stage, and/or become a good quality blastocyst and/or implant into the uterus and/or be euploid or aneuploid. The terms "reference" and "control" as used herein mean a standardized embryo or cell to be used to interpret the cell parameter measurements of a given embryo and assign a determination of the likelihood of the embryo to reach or not reach the blastocyst stage, and/or become a good quality blastocyst and/or implant into the uterus and/or be euploid or aneuploid. The reference or control may be an embryo that is known to have a desired phenotype, e.g., likely to reach the blastocyst stage, and/or become a good quality blastocyst and/or implant into the uterus and/or be euploid, and therefore may be a positive reference or control embryo. Alternatively, the reference/control embryo may be an embryo known to not have the desired phenotype, and therefore be a negative reference/control embryo.

In certain embodiments, cellular parameters are first employed to determine whether an embryo will be likely to reach the blastocyst stage, and/or become a good quality blastocyst and/or implant into a uterus and/or be euploid. In such embodiments, embryos that fall within one or more of the above referenced cellular parameter time frames (e.g. a time between cytokinesis 1 and cytokinesis 2 of about 7.8 to about 14.3 hours and/or a time between cytokinesis 2 and cytokinesis 3 of about 0 to about 5.8 hours) is selected to have good developmental potential and/or be euploid. These embryos are then analyzed to determine if they have a normal syngamy or abnormal syngamy. Embryos previously selected to have good developmental potential and/or be euploid are deselected when they are determined to have AS or US, thereby selecting for implantation or freezing for potential future implantation, only those embryos that fall within the selection criteria and outside the deselection criteria. Similarly, embryos determined to have good developmental potential and/or be euploid are deselected as being likely to be aneuploid when $P_{syn}$ is measured to be less than about 2.4 hours, or less than about 2.3 hours or less than about 2 hours or less than about 1.5 hours or less than about an hour.

In certain embodiments, the obtained cell parameter measurement(s) is compared to a comparable cell parameter measurement(s) from a single reference/control embryo to obtain information regarding the phenotype of the embryo/cell being assayed. In yet other embodiments, the obtained cell parameter measurement(s) is compared to the comparable cell parameter measurement(s) from two or more different reference/control embryos to obtain more in depth information regarding the phenotype of the assayed embryo/cell. For example, the obtained cell parameter measurements from the embryo(s) being assessed may be compared to both a positive and negative embryo to obtain confirmed information regarding whether the embryo/cell has the phenotype of interest.

As an example, the resolution of cytokinesis 1 and the onset of cytokinesis 2 in normal human embryos is about 8-15 hours, more often about 9-13 hours, with an average value of about 11+/−2.1 hours; i.e. 6, 7, or 8 hours, more usually about 9, 10, 11, 12, 13, 14 or up to about 15 hours. A longer or shorter cell cycle 2 in the embryo being assessed as compared to that observed for a normal reference embryo is indicative of the likelihood that the embryo will not reach the blastocyst stage and/or implant into the uterus and/or is more likely to be aneuploid. As a second example, the time interval between the initiation of cytokinesis 2 and the initiation of cytokinesis 3, i.e. the synchronicity of the second and third mitosis, in normal human embryos is usually about 0-5 hours, more usually about 0, 1, 2 or 3 hours, with an average time of about 1+/−1.6 hours; a longer interval between the completion of cytokinesis 2 and cytokinesis 3 in the embryo being assessed as compared to that observed in a normal reference embryo is indicative of the likelihood that the embryo will not reach the blastocyst stage and/or implant into the uterus and/or is more likely to be aneuploid. As a third example, cell cycle 1 in a normal embryo, i.e. from the time of fertilization to the completion of cytokinesis 1, is typically completed in about 20-27 hours, more usually in about 25-27 hours, i.e. about 15, 16, 17, 18, or 19 hours, more usually about 20, 21, 22, 23, or 24 hours, and more usually about 25, 26 or 27 hours. A cell cycle 1 that is longer in the embryo being assessed as compared to that observed for a normal reference embryo is indicative of the likelihood that the embryo will not reach the blastocyst stage and/or implant into the uterus and/or is more likely to be aneuploid. As a fourth example, embryos that display NS including those that, for example, display minimal pronuclear movement within the cytoplasm and/or minimal oolema movement prior to PN envelope dispersion and/or begin a first cytokinesis 1 about 2.5-4 (e.g. 2.5, 3, or 4 hours) hours after syngamy are more likely to reach the blastocyst stage whereas embryos that display AS, including those, for example, that display disordered PN moment without prompt dispersion of nuclear envelopes and/or display active oolema movement prior to PN envelope dispersion including those that begin a first cytokinesis about 1 hour or less after syngamy are less likely to reach the blastocyst stage and/or develop into good quality blastocysts and/or are more likely to be aneuploid. Examples may be derived from empirical data, e.g. by observing one or more reference embryos alongside the embryo to be assessed. Any reference embryo may be employed, e.g. a normal reference that is likely to reach the blastocyst stage, and/or develop into a good quality blastocyst and/or implant into the uterus and/or be euploid, or an atypical reference sample that is not likely to reach the blastocyst stage and/or is more likely to be aneuploid. In some cases, more than one reference sample may be employed, e.g. both a normal reference sample and an atypical reference sample may be used.

As discussed above, one or more parameters may be measured and employed to determine the likelihood of reaching the blastocyst stage for an embryo. In some embodiments, a measurement of two parameters may be sufficient to arrive at a determination of the likelihood of reaching the blastocyst stage and/or becoming a good quality blastocyst and/or implant into the uterus and/or be euploid. In some embodiments, it may be desirable to employ measurements of more than two parameters, for example, 3 cellular parameters or 4 or more cellular parameters. In some embodiments, it may be desirable to measure one or more parameters for selecting an embryo with good developmental potential and one or more parameters for deselecting embryos with poor developmental potential. In certain embodiments, 1 selection parameter and 1 deselection parameter is measured. In another embodiment, 1 selection parameter and 2 deselection parameters are measured. In another embodiment, 1 selection parameter and 3 deselection parameters are measured. In another embodiment, 2 selection parameters and 1 deselection parameter are measured. In another embodiment, 3 selection parameter and 1 deselection parameter are measured. In another embodiment, more than 3 selection parameters and 1 deselection parameter are measured. In another embodiment, 2 selection parameters and 2 deselection parameters are measured. In another embodiment, 2 selection parameters and 3 deselection parameters are measured. In another embodiment, 3 selection parameters and 2 deselection parameters are measured. In another embodiment, more than 3 selection parameters and 2 deselection parameters are measured. In another embodiment, more than 3 selection parameters and 3 deselection parameters are measured.

In certain embodiments, assaying for multiple parameters may be desirable as assaying for multiple parameters may provide for greater sensitivity and specificity. By sensitivity it is meant the proportion of actual positives which are correctly identified as being such. This may be depicted mathematically as:

$$\text{Sensitivity} = \frac{(\text{Number of true positives})}{(\text{Number of true positives} + \text{Number of false negatives})}$$

Thus, in a method in which "positives" are the embryos that have good developmental potential, i.e. that will develop into blastocysts, and/or become a good quality blastocyst and/or implant into the uterus and/or be euploid, and "negatives" are the embryos that have poor developmental potential, i.e. that will not develop into blastocysts nor develop into good quality blastocysts or implant into the uterus and/or are aneuploid a sensitivity of 100% means that the test recognizes all embryos that will develop into blastocysts, or become good quality blastocysts or implant in to the uterus and/or be eupliod as such. In some embodiments, the sensitivity of the assay may be about 70%, 80%, 90%, 95%, 98% or more, e.g. 100%. By specificity it is meant the proportion of "negatives" which are correctly identified as such. As discussed above, the term "specificity" when used herein with respect to prediction and/or evaluation methods is used to refer to the ability to predict or evaluate an embryo for determining the likelihood that the embryo will not develop into a blastocyst, nor become a good quality blastocyst or implant into the uterus and/or be euploid by assessing, determining, identifying or selecting embryos that are not likely to reach the blastocyst stage and/or become a good quality blastocyst and/or implant into the uterus or those that are more likely to be aneuploid. This may be depicted mathematically as:

$$\text{Specificity} = \frac{(\text{Number of true negatives})}{(\text{Number of true negatives} + \text{Number of false positives})}$$

Thus, in a method in which positives are the embryos that are likely to reach the blastocyst stage and/or become good quality blastocysts and/or implant into the uterus (i.e., that are likely to develop into blastocysts) and/or be euploid and negatives are the embryos that are likely not to reach the blastocyst stage (i.e., that are not likely to develop into blastocysts) or those that are more likely to be aneuploid a specificity of 100% means that the test recognizes all embryos that will not develop into blastocysts, i.e. will arrest prior to the blastocyst stage. In some embodiments, the specificity can be a "high specificity" of 70%, 72%, 75%, 77%, 80%, 82%, 85%, 88%, 90%, 92%, 95%, 98% or more, e.g. 100%. As demonstrated in the examples sections below, the use of two parameters provides sensitivity of 40%, 57%, 68%, 62%, 68% and specificity of 86%, 88%, 83%, 83%, 77%, respectively. In other words, in one exemplary embodiment, the methods of the invention are able to correctly identify the number of embryos that are going to develop into blastocysts and/or be euploid at least about 40%-68% of the time (sensitivity), and the number of embryos that are going to arrest before the blastocyst stage and/or be aneuploid at least about 77%-88% of the time (specificity), regardless of the algorithm model employed, and as such the present invention provides a high specificity method for identifying the embryos that will arrest before the blastocyst stage or not develop into good quality blastocysts and/or be aneuploid. In addition, the specified mean values and/or cut-off points may be modified depending upon the data set used to calculate these values as well as the specific application.

In some embodiments, the assessment of an embryo or includes generating a written report that includes the artisan's assessment of the subject embryo, e.g. "assessment/selection/determination of embryos likely and/or not likely to reach the blastocyst stage and/or develop into good quality blastocysts and/or implant into the uterus", an "assessment of chromosomal abnormalities", etc. Thus, a subject method may further include a step of generating or outputting a report providing the results of such an assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to an assessment arrived at by methods of the invention. A subject report can be completely or partially electronically generated. A subject report includes at least an assessment of the likelihood of the subject embryo or to reach the blastocyst stage and/or implant into the uterus, an assessment of the probability of the existence of chromosomal abnormalities, etc. A subject report can further include one or more of: 1) information regarding the testing facility; 2) service provider information; 3) subject data; 4) sample data; 5) a detailed assessment report section, providing information relating to how the assessment was arrived at, e.g. a) cell parameter measurements taken, b) reference values employed, if any; and 6) other features.

The report may include information about the testing facility, which information is relevant to the hospital, clinic, or laboratory in which sample gathering and/or data generation was conducted. Sample gathering can include how the sample was generated, e.g. how it was harvested from a subject, and/or how it was cultured etc. Data generation can include how images were acquired or gene expression profiles were analyzed. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents or culture media (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample preparation and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including medical history of subjects from which oocytes or were harvested, patient age, in vitro fertilization cycle characteristics (e.g. fertilization rate, day 3 follicle stimulating hormone (FSH) level), and, when oocytes are harvested, zygote/embryo cohort parameters (e.g. total number of embryos). This subject data may be integrated to improve embryo assessment and/or help determine the optimal number of embryos to transfer. The report may also include administrative subject data (that is, data that are not essential to the assessment of the likelihood of reaching the blastocyst stage) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the assessment of developmental potential and, if different from the ordering physician, the name of a staff physician who is responsible for the subject's care (e.g., primary care physician).

The report may include a sample data section, which may provide information about the biological sample analyzed in the assessment, such as how the sample was handled (e.g. storage temperature, preparatory protocols) and the date and time collected. Report fields with this information can generally be populated using data entered by the user, some of which may be provided as pre-scripted selections (e.g., using a drop-down menu).

The report may include an assessment report section, which may include information relating to how the assessments/determinations were arrived at as described herein. The interpretive report can include, for example, time-lapse images of the embryo being assessed, and/or gene expression results. The assessment portion of the report can optionally also include a recommendation(s) section. For example, where the results indicate that the embryo is likely to reach the blastocyst stage and/or implant into the uterus, the recommendation can include a recommendation that a limited number of embryos be transplanted into the uterus during fertility treatment as recommended in the art.

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, etc.

It will be readily appreciated that the report can include all or some of the elements above, with the proviso that the report generally includes at least the elements sufficient to provide the analysis requested by the user (e.g., an assessment of the likelihood of reaching the blastocyst stage).

As discussed above, methods of the invention may be used to assess embryos or cells to determine the likelihood of the embryos to reach the blastocyst stage, and/or develop into good quality blastocysts and/or implant into the uterus and/or be euploid. This determination of the likelihood of the embryos or to reach the blastocyst stage and/or implant into the uterus may be used to guide clinical decisions and/or actions. For example, in order to increase pregnancy rates, clinicians often transfer multiple embryos into patients, potentially resulting in multiple pregnancies that pose health risks to both the mother and fetuses. Using results obtained from the methods of the invention, the likelihood of reaching the blastocyst stage, and/or develop into good quality blastocysts and/or implant into the uterus and/or be euploid can be determined for embryos being transferred. As the embryos or that are likely to reach the blastocyst stage, and/or develop into good quality blastocysts and/or implant into the uterus and/or be euploid are more likely to develop into fetuses, the determination of the likelihood of the embryo to reach the blastocyst stage, and/or develop into good quality blastocysts and/or implant into the uterus and/or be euploid prior to transplantation allows the practitioner to decide how many embryos to transfer so as to maximize the chance of success of a full term pregnancy while minimizing risk.

Assessments made by following methods of the invention may also find use in ranking embryos or in a group of embryos or for their likelihood that the embryos or will reach the blastocyst stage as well as for the quality of the blastocyst and ploidy status (euploid or aneuploid) that will be achieved (e.g., in some embodiments this would include the likelihood of implanting into the uterus). For example, in some instances, multiple embryos may be capable of developing into blastocysts, i.e. multiple embryos are likely to reach the blastocyst stage. However, some embryos will be more likely to achieve the blastocyst stage, i.e. they will have better likelihood to reach the blastocyst stage, or better likelihood to develop into good quality blastocyst, or better likelihood to implant into the uterus than other embryos or may be more likely to be euploid. In such cases, methods of the invention may be used to rank the embryos in the group. In such methods, one or more cellular parameters for each embryo is measured to arrive at a cell parameter measurement for each embryo. The one or more cell parameter measurements from each of the embryos are then employed to determine the likelihood of the embryos relative to one another to reach the blastocyst stage and/or to implant into the uterus and/or be euploid. In some embodiments, the cell parameter measurements from each of the embryos or are employed by comparing them directly to one another to determine the likelihood of reaching the blastocyst stage and/or implant into the uterus and/or be euploid. In some embodiments, the cell parameter measurements from each of the embryos are employed by comparing the cell parameter measurements to a cell parameter measurement from a reference embryo to determine likelihood of reaching the blastocyst stage and/or implant into the uterus for each embryo, and then comparing the determination of the likelihood of reaching the blastocyst stage and/or implant into the uterus and/or be euploid for each embryo to determine the likelihood of reaching the blastocyst stage and/or implant into the uterus and/or be euploid of the embryos or relative to one another.

In this way, a practitioner assessing, for example, multiple zygotes/embryos, can choose only the best quality embryos, i.e. those with the best likelihood of reaching the blastocyst stage and/or implant into the uterus and/or of being euploid, to transfer so as to maximize the chance of success of a full term pregnancy while minimizing risk.

Also provided are reagents, devices and kits thereof for practicing one or more of the above-described methods. The subject reagents, devices and kits thereof may vary greatly. Reagents and devices of interest include those mentioned above with respect to the methods of measuring any of the aforementioned cellular parameters, where such reagents may include culture plates, culture media, microscopes, imaging software, imaging analysis software, nucleic acid primers, arrays of nucleic acid probes, antibodies, signal producing system reagents, etc., depending on the particular measuring protocol to be performed.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Some of the methods described above require the ability to observe embryo development via time-lapse imaging. This can be achieved using a system comprised of a miniature, multi-channel microscope array that can fit inside a standard incubator. This allows multiple samples to be imaged quickly and simultaneously without having to physically move the dishes. One illustrative prototype, shown in FIG. 22 of U.S. Pat. No. 7,963,906 (See also PCT/US2011/053537), consists of a 3-channel microscope array with darkfield illumination, although other types of illumination could be used. By "three channel," it is meant that there are three independent microscopes imaging three distinct culture dishes simultaneously. A stepper motor is used to adjust the focal position for focusing or acquiring 3D image stacks. White-light LEDs are used for illumination, although we have observed that for human embryos, using red or near-infrared (IR) LEDs can improve the contrast ratio between cell membranes and the inner portions of the cells. This improved contrast ratio can help with both manual and automated image analysis. In addition, moving to the infrared region can reduce phototoxicity to the samples. Images are captured by low-cost, high-resolution webcams, but other types of cameras may be used.

As shown in FIG. 22 of U.S. Pat. No. 7,963,906 (See also PCT/US2011/053537), each microscope of the prototype system described above is used to image a culture dish which may contain anywhere from 1-30 embryos. The microscope collects light from a white light LED connected to a heat sink to help dissipate any heat generated by the LED, which is very small for brief exposure times. The light passes through a conventional dark field patch for stopping direct light, through a condenser lens and onto a specimen labeled "petri dish," which is a culture dish holding the embryos being cultured and studied. The culture dish may have wells that help maintain the order of the embryos and keep them from moving while the dish is being carried to and from the incubator. The wells can be spaced close enough together so that embryos can share the same media drop. The scattered light is then passed through a microscope objective, then through an achromat doublet, and onto a CMOS sensor. The CMOS sensor acts as a digital camera and is connected to a computer for image analysis and tracking as described above.

This design is easily scalable to provide significantly more channels and different illumination techniques, and can be modified to accommodate fluidic devices for feeding the samples. In addition, the design can be integrated with a feedback control system, where culture conditions such as temperature, $CO_2$ (to control pH), and media are optimized in real-time based on feedback and from the imaging data. This system was used to acquire time-lapse videos of human embryo development, which has utility in determining embryo viability for in vitro fertilization (IVF) procedures. Other applications include stem cell therapy, drug screening, and tissue engineering.

In one embodiment of the device, illumination is provided by a Luxeon white light-emitting diode (LED) mounted on an aluminum heat sink and powered by a BuckPuck current regulated driver. Light from the LED is passed through a collimating lens. The collimated light then passes through a custom laser-machined patch stop, as shown in FIG. 22 of U.S. Pat. No. 7,963,906 (See also PCT/US2011/053537), and focused into a hollow cone of light using an aspheric condenser lens. Light that is directly transmitted through the sample is rejected by the objective, while light that is scattered by the sample is collected. In one embodiment, Olympus objectives with 20× magnification are used, although smaller magnifications can be used to increase the field-of-view, or larger magnifications can be used to increase resolution. The collected light is then passed through an achromat doublet lens (i.e. tube lens) to reduce the effects of chromatic and spherical aberration. Alternatively, the collected light from the imaging objective can be passed through another objective, pointed in the opposing direction that acts as a replacement to the tube lens. In one configuration, the imaging objective can be a 10× objective, while the tube-lens objective can be a 4× objective. The resulting image is captured by a CMOS sensor with 2 megapixel resolution (1600×1200 pixels). Different types of sensors and resolutions can also be used.

For example, FIG. 23A of U.S. Pat. No. 7,963,906 (See also PCT/US2011/053537) shows a schematic of the multi-channel microscope array having 3 identical microscopes. All optical components are mounted in lens tubes. In operation of the array system, Petri dishes are loaded on acrylic platforms that are mounted on manual 2-axis tilt stages, which allow adjustment of the image plane relative to the optical axis. These stages are fixed to the base of the microscope and do not move after the initial alignment. The illumination modules, consisting of the LEDs, collimator lenses, patch stops, and condenser lenses, are mounted on manual xyz stages for positioning and focusing the illumination light. The imaging modules, consisting of the objectives, achromat lenses, and CMOS sensors, are also mounted on manual xyz stages for positioning the field-of-view and focusing the objectives. All 3 of the imaging modules are attached to linear slides and supported by a single lever arm, which is actuated using a stepper motor. This allows for computer-controlled focusing and automatic capture of image-stacks. Other methods of automatic focusing as well as actuation can be used.

The microscope array was placed inside a standard incubator, as shown in, for example, FIG. 23B of U.S. Pat. No. 7,963,906 (See also PCT/US2011/053537). The CMOS image sensors are connected via USB connection to a single hub located inside the incubator, which is routed to an external PC along with other communication and power lines. All electrical cables exit the incubator through the center of a rubber stopper sealed with silicone glue.

The above described microscope array, or one similar, can be used to record time-lapse images of early human embryo development and documented growth from zygote through blastocyst stages. In some embodiments, images can be captured every 5 minutes with roughly 1 second of low-light exposure per image. The total amount of light received by the samples can be equivalent to 52 seconds of continuous exposure, similar to the total level experienced in an IVF clinic during handling. The 1 second duration of light exposure per image can in some embodiments be reduced. Prior to working with the human embryos, we performed extensive control experiments with mouse pre-implantation embryos to ensure that both the blastocyst formation rate and gene expression patterns were not affected by the imaging process.

Individual embryos can be followed over time, even though their positions in the photographic field shifted as the embryos underwent a media change, in some cases the media was changed at day 3. The use of sequential media may be needed to meet the stage-specific requirements of the developing embryos. During media change, the embryos were removed from the imaging station for a few minutes and transferred to new petri dishes. The issue of tracking embryo identity can be mitigated by using wells to help arrange the embryos in a particular order.

When transferring the petri dishes between different stations, the embryos can sometimes move around, thereby making it difficult to keep track of embryo identity. This poses a challenge when time-lapse imaging is performed on one station, and the embryos are subsequently moved to a second station for embryo selection and transfer. One method is to culture embryos in individual petri dishes. However, this requires each embryo to have its own media drop. In a typical IVF procedure, it is usually desirable to culture all of a patient's embryos on the same petri dish and in the same media drop. To address this problem, we have designed a custom petri dish with micro-wells. This keeps the embryos from moving around and maintains their arrangement on the petri dish when transferred to and from the incubator or imaging stations. In addition, the wells are small enough and spaced closely together such that they can share the same media drop and all be viewed simultaneously by the same microscope. The bottom surface of each micro-well has an optical quality finish. For example, FIG. 27A in U.S. Pat. No. 7,963,906 shows a drawing with dimensions for one exemplary embodiment. In this version, there are 25 micro-wells spaced closely together within a 1.7×1.7 mm field-of-view. FIG. 27B of U.S. Pat. No. 7,963,906 shows a 3D-view of the micro-wells, which are recessed approximately 100 microns into the dish surface. Fiducial markers, including letters, numbers, and other markings, are included on the dish to help with identification. All references cited herein, including patents, patent applications, manuscripts and the like are specifically and fully incorporated by reference in their entireties.

EXAMPLES

The following examples are put forth so as to provide those of ordinary skill in the art with a disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A retrospective cohort study was done using image data collected from 651 embryos from 67 patients from five clinics in a 16 month period. Patient embryos were imaged using the EEVA™ Test, a time-lapse technology developed for blastocyst prediction.

All imaged embryos were identified as having 2 pronuclei (PN) before being placed in a multi-well EEVA™ dish that allows embryos to be tracked individually while sharing a single drop of culture media. A fertilization check was performed according to each clinic's standard protocol. All 2PN embryos were transferred to the EEVA™ dish immediately after fertilization status was assessed, and the dish was placed on the EEVA™ scope in the incubator. To maintain a continuous and uninterrupted imaging process from Day 1 through Day 3, no media changes or dish removal from the incubator were permitted. On Day 3, imaging was stopped just before routine embryo grading was performed. All embryos were tracked individually to maintain their identities. Embryo grading, selection and transfer (on Days 3 or 5), were performed according to the standard operating procedures of each individual clinic.

Embryo development outcome was measured by overall morphology grade and blastocyst formation rate. The overall embryo grade was determined using cleavage stage and blastocyst stage morphological grading as defined by the Society for Assisted Reproductive Technology (SART) (Racowsky, C., et al., Fertil Steril, 2010. 94(3): p. 1152-3; Vernon, M., et al., Fertil Steril, 2011. 95(8): p. 2761-3). Further discrimination among the Day 3 embryos with 6-10 cells was included in the analysis to focus on the top quality embryos with ≤10% fragmentation. Implantation was confirmed by ultrasound showing evidence of intrauterine fetal heart motion at approximately 6-8 weeks gestational age. Known implantation included data in which the embryo implantation status was confirmed, e.g., number of gestational sacs matched the number of transferred embryos.

Mean values were compared using a t-test using SAS. Associations between presence or absence of atypical phenotypes and embryo quality and development potential were examined using a chi-squared test or Fisher's Exact test to assess statistical significance, where p<0.05 was considered to be statistically significant.

Embryo videos were reviewed and evaluated for AS and $P_{syn}$.

Embryos with timely disappearance of pronuclei (PN) and smooth dispersion of the nuclear envelopes were categorized as normal syngamy (NS), or control. Embryos with disordered PN movement within the cytoplasm without prompt dispersion of the nuclear envelopes were categorized as AS. $P_{syn}$, the time from syngamy to the first cytokinesis, was also measured in embryos where syngamy could be measured. Embryos were categorized as immeasurable where syngamy was not measurable.

The overall prevalence of AS was 25.1% (163/649) among all embryos reviewed, and prevalent in 73.0% (49/67) patients. The mean time for $P_{syn}$ was significantly shorter for embryos exhibiting AS vs. NS (1.8±1.4 hours vs. 2.4±1.8 hours, p<0.0001). Compared to NS embryos, AS embryos tend to have poorer morphology grading on day 3 (6-10 cells and ≤10% fragmentation, 41.6% vs. 61.7%, p=0.002), fewer cleavage embryos with overall grade good or fair (78.6% vs. 90.7%, p<0.001), and a higher rate of high fragmentation (>25% fragmentation, 12.4% (11/89) vs. 8.4% (29/345), p<0.0001) (Table 2). Although both NS and AS embryos had a similar percentage of embryos cultured to day 5 (65.6% (107/163) vs. 66.0% (292/443), p=0.5), notably, the blastocyst formation rate was significantly lower for AS embryos (21.5% vs. 44.9%, p<0.0001) and most AS embryos that formed blastocysts were poor quality. Only 26.4% of the AS embryos were transferred or frozen, while 50.1% of the NS embryos were selected. Analysis of the known implantation data revealed implantation rates of 0.0% for AS embryos and 17.9% for NS embryos (p=0.08).

different distribution (p=0.001, Wilcoxon-Mann-Whitney test) between aneuploid embryos (2.34±0.44 hours, n=128) and euploid embryos (2.50±0.51 hours, n=274).

These data show that $P_{syn}$ can be used to provide a probability estimate for embryo aneuploidy. A longer $P_{syn}$ can be used to select embryos that are more likely to be euploid, whereas a shorter $P_{syn}$ can be used to deselect embryos that are more likely to be aneuploid. Thus, $P_{syn}$ may be used alone, or in combination with previously described parameters, such as those described in U.S. Pat. Nos. 7,963,906; 8,323,177, and 8,337,387 and PCT Appl. No.: WO 2012/163363 to select embryos that are most likely to reach blastocyst and/or implant into the uterus and deselect embryos that are likely to not reach blastocyst and/or implant into the uterus.

TABLE 2

Abnormal Syngamy (AS): Embryo Quality and Developmental Potential for Day 3 and Day 5 Embryos.

| Abnormal Syngamy (AS) | Day 3 6-10 cells ≤10% frag | Day 3 Overall Grade Good/Fair | Blastocyst Formation Rate | Blastocyst Overall Grade Good/Fair | Transferred or Frozen Embryos | Known Implantation Data |
|---|---|---|---|---|---|---|
| Control: Without AS (n = 443) | 61.7% (213/345) | 90.7% (313/345) | 44.9% (131/292) | 60.0% (79/131) | 50.1% (222/443) | 17.9% (19/106) |
| With AS (n = 163) | 41.6% (37/89) | 78.6% (70/89) | 21.5% (23/107) | 30.0% (7/23) | 26.4% (43/163) | 0.0% (0/14) |
| p-value | <0.001 | 0.002 | <0.0001 | 0.008 | <0.0001 | 0.08 |

Taken together, these data clearly show that AS embryos reach the blastocyst stage at a much lower rate than NS embryos and those that do reach blastocyst are of much poorer quality demonstrating that these novel syngamy parameters provide for an early indicator of embryos with low developmental potential. Thus, these parameters may be used alone, or in combination with previously described parameters, such as those described in U.S. Pat. Nos. 7,963,906; 8,323,177, and 8,337,387 and PCT Appl. No.: WO 2012/163363 to select embryos that are most likely to reach blastocyst and/or implant into the uterus and deselect embryos that are likely to not reach blastocyst and/or implant into the uterus.

Example 2

It has been reported that more than 50% of the human embryos cultured in IVF clinics are aneuploid embryos that have an abnormal number of chromosomes. These aneuploid embryos have lower implantation rates and are not likely to result in live birth of healthy babies. Currently, pre-implantation genetic screening (PGS) is the most effective approach to select against aneuploidy embryos. However, due to its high cost, labor intensive requirements and invasive nature, less than 10% of patients that are treated for assisted reproduction undergo PGS prior to embryo transfer.

In order to develop a non-invasive time-lapse enabled assay to assess the risk of embryos being aneuploid, it was discovered that by assessing the $P_{syn}$ parameter, alone or in combination with other cellular parameter, embryo morphology and patient information, the likelihood of an embryo being aneuploid can be determined.

Figure 3:
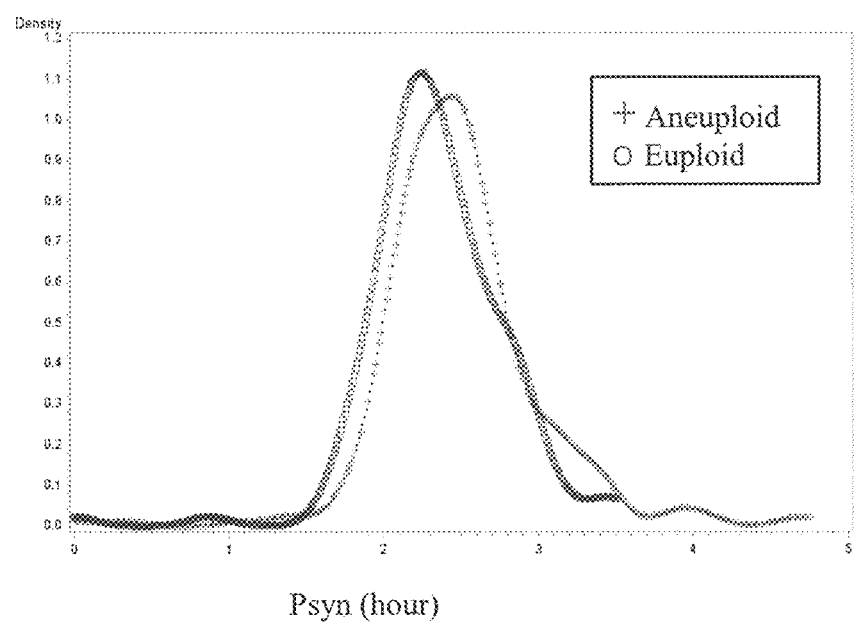
FIG. 3 is a kernel density estimation (KDE) graph that shows time of syngamy to first cytokinesis ($P_{syn}$) for euploid (o) and aneuploid (+) embryos.
Figure 4:
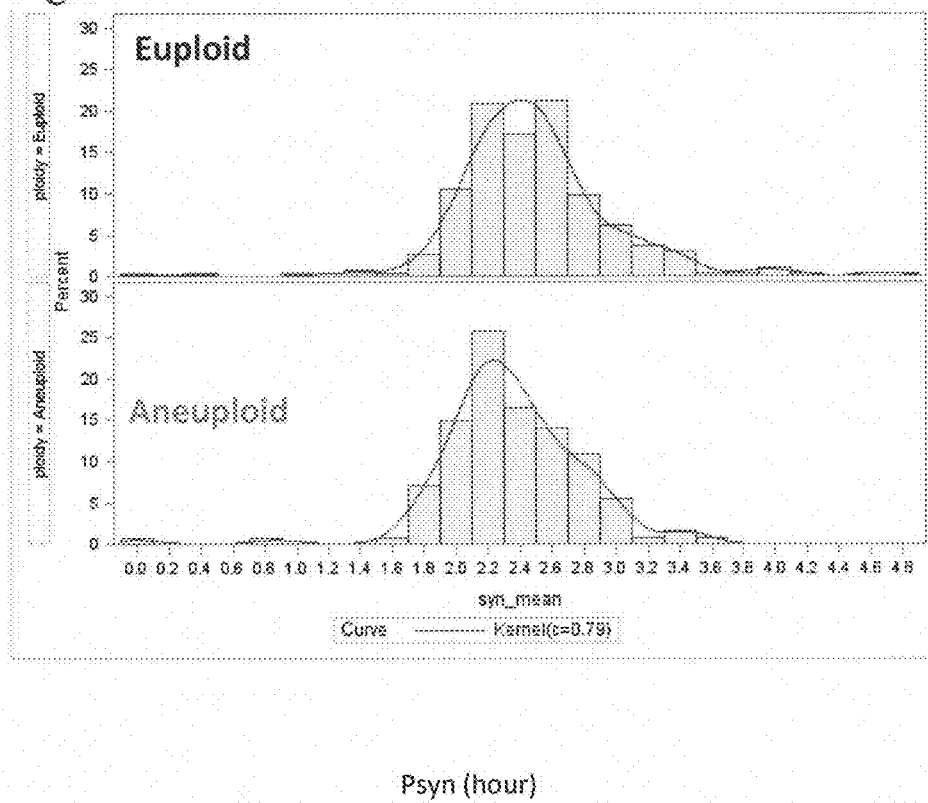
FIG. 4 is a histogram plot with kernel estimation that shows time of syngamy to first cytokinesis ($P_{syn}$) for euploid (top) and aneuploid (bottom) embryos.

By evaluating $P_{syn}$ values from time-lapse data of 402 embryos, it was discovered that euploid embryos have longer $P_{syn}$ than aneuploid embryos. As shown in FIGS. 3 and 4, the $P_{syn}$ parameter has a statistically significant Example 3

Further analysis of the retrospective cohort study described in the previous examples was performed to evaluate the AS parameters in combination with other atypical phenotype parameters. Using the data from the 67 patients and 639 embryo movies, embryos with one or more atypical phenotypes were analyzed.

The atypical phenotypes examined were abnormal cleavage (AC), abnormal syngamy (AS), abnormal first cytokinesis ($A1^{cyt}$), and chaotic cleavage. The AS phenotype was defined as described in Example 1. The AC phenotype was defined as embryos exhibiting producing more than 2 cells during a single cell division event, including AC1 phenotypes that exhibited a first cleavage yielding more than two blastomeres and AC2 phenotypes that exhibited a daughter cell cleavage yielding more than two blastomeres. The $A1^{cyt}$ phenotype was defined as embryos exhibiting oolema ruffling with or without the formation of pseudo furrows before the completion of first cytokinesis. The chaotic cleavage phenotype was defined as embryos exhibiting disordered cleavage behavior, with or without the presence of many fragments by the 4-cell stage.

The overall prevalence of embryos exhibiting one or more atypical phenotype(s) was 54.2% among all embryos reviewed and prevalent in 98.5% (66/67) among all patient cases. Compared to the control group (without any atypical phenotype), embryos with at least one atypical phenotype tended to have fewer good quality embryos on Day 3 (6-10 cells and ≤10% fragmentation, 45.4% vs. 67.8%, p<0.0001), higher rate of embryos highly fragmented (>25% fragmentation, 28.4% (100/352) vs. 5.74% (17/297) p<0.0001) and fewer cleavage embryos with overall grade good or fair (80.3% vs. 94.7%, p<0.0001) (Table 3). Both groups presented similar blastocyst formation rate (52.1% vs. 56.9%, p=0.6) and similar percentages of good or fair quality blastocysts (52.1% vs. 56.9%, p=0.6), but had statistically significant differences in the number of transferred or frozen embryos (34.7% vs. 53.9%, p<0.0001). Embryos with at least one phenotype also had a statistically significant lower implantation rate (8.6% vs. 21.9%, p=0.02).

TABLE 3

Embryos displaying one or more atypical phenotype(s): Embryo Quality and Developmental Potential for Day 3 and Day 5 Embryos.

| One or more atypical phenotypes | Day 3 6-10 cells ≤10% frag | Day 3 Overall Grade Good/Fair | Blastocyst Formation Rate | Blastocyst Overall Grade Good/Fair | Transferred or Frozen Embryos | Known Implantation Data |
| --- | --- | --- | --- | --- | --- | --- |
| Control: Without any atypical phenotype (n = 297) | 67.8% (166/245) | 94.7% (232/245) | 53.7% (109/203) | 56.9% (62/109) | 53.9% (160/297) | 21.9% (16/64) |
| With one or more atypical phenotypes (n = 352) | 45.4% (99/218) | 80.3% (175/218) | 22.4% (48/214) | 52.1% (25/48) | 34.7% (122/352) | 8.6% (5/58) |
| p-value | <0.0001 | <0.0001 | <0.0001 | 0.6 | <0.0001 | 0.02 |

The group of embryos displaying one or more atypical phenotypes was statistically significantly different than the control group for most outcomes. Remarkably, 5 in every 10 embryos showed at least one atypical phenotype: 18.8% of the embryos showed at least 2 phenotypes (122/649), 6.5% showed 3 phenotypes (42/649) and 1.1% showed 4 phenotypes (7/649). This extraordinarily high prevalence within embryo cohorts suggests that tools to deselect these dynamic phenomena are urgently needed to increase the chances of selecting a competent embryo, particularly as this study has demonstrated that many embryos exhibiting normal phenotypes have good conventional morphology on day 3 and day 5.

The invention claimed is:

1. A method for treating infertility in a female human subject, comprising:
   (A) providing one or more human embryos under in vitro culture conditions sufficient for embryo development;
   (B) imaging said one or more human embryos for a time period from at least syngamy to at least a first cytokinesis to create images, wherein said one or more human embryos comprise at least one cellular parameter;
   (C) identifying one or more abnormal syngamy (AS) embryos when said time period is less than 2.5 hours and one or more normal syngamy (NS) embryos when said time period is greater than 2.5 hours;
   (D) deselecting said one or more human embryos when at least one of said images comprises said one or more AS embryos;
   (E) selecting said one or more human embryos when at least one of said images comprises said one or more NS embryos; and
   (F) developing at least one of said selected NS embryos under said in vitro culture conditions into a normal human blastocyst embryo; and
   (G) treating infertility of a female human subject with said normal human blastocyst embryo by in vitro fertilization.

2. The method of claim 1 wherein said at least one cellular parameter is selected from the group consisting of:
   (a) the duration of the first cytokinesis;
   (b) the time between the first and second mitosis;
   (c) the time between the second and third mitosis;
   (d) the time interval between cytokinesis 1 and cytokinesis 2;
   (e) the time interval between cytokinesis 2 and cytokinesis 3;
   (f) the time interval between fertilization and the 5 cell stage; and
   (g) the duration of the first cell cycle.

3. The method of claim 1 wherein said one or more human embryos are produced by fertilization of oocytes in vitro.

4. The method of claim 3 wherein said oocytes are matured in vitro.

5. The method of claim 4 wherein said oocytes matured in vitro are supplemented with growth factors.

6. The method of claim 1 wherein said one or more human embryos have not been frozen prior to said providing.

7. The method of claim 1 wherein said one or more human embryos have been frozen prior to said providing.

8. The method of claim 1 wherein said selecting of said normal human embryo is automated.

9. The method of claim 1 wherein said images are digitally stored.

10. The method of claim 1 wherein said imaging employs darkfield illumination.

11. The method of claim 1 wherein said one or more human embryos are provided in a culture dish.

12. The method of claim 11 wherein said culture dish comprises a plurality of microwells.

13. The method of claim 12 wherein said culture dish comprises up to about 30 microwells.

14. The method of claim 12 wherein said one or more human embryos is provided in at least one of said plurality of microwells.

15. The method of claim 1 wherein the imaging is carried out at an imaging station.

16. The method of claim 1, wherein said AS embryo further comprises said at least one cellular parameter selected from the group consisting of a disordered pronuclei movement, a delayed dispersion of nuclear envelopes, and an active oolema movement before the dispersion of the nuclear envelopes.

17. The method of claim 1, wherein said NS embryo further comprises said at least one cellular parameter selected from the group consisting of a timely disappearance of pronuclei, a smooth dispersion of the nuclear envelopes, a minimal or no pronuclear movement within the cytoplasm, a minimal or no oolema movement before the dispersion of nuclear envelopes and a first cytokinesis duration is about 0-33 minutes.

* * * * *